(12) United States Patent
Meyer

(10) Patent No.: US 10,302,625 B2
(45) Date of Patent: May 28, 2019

(54) PERIPHERAL MEASURE OF CENTRAL BRAIN INFLAMMATION, MARKERS THEREFOR AND USES THEREOF

(71) Applicant: CENTRE FOR ADDICTION AND MENTAL HEALTH, Toronto, Ontario (CA)

(72) Inventor: Jeff Meyer, Toronto (CA)

(73) Assignee: Centre for Addiction and Mental Health, Toronto, Ontario (CA)

( * ) Notice: Subject to any disclaimer, the term of this patent is extended or adjusted under 35 U.S.C. 154(b) by 0 days.

(21) Appl. No.: 15/543,914

(22) PCT Filed: Jan. 15, 2016

(86) PCT No.: PCT/CA2016/050036
§ 371 (c)(1),
(2) Date: Jul. 14, 2017

(87) PCT Pub. No.: WO2016/112467
PCT Pub. Date: Jul. 21, 2016

(65) Prior Publication Data
US 2018/0267015 A1    Sep. 20, 2018

Related U.S. Application Data

(60) Provisional application No. 62/103,773, filed on Jan. 15, 2015.

(51) Int. Cl.
| G01N 33/53 | (2006.01) |
| G01N 33/49 | (2006.01) |
| G01N 33/48 | (2006.01) |
| G01N 33/88 | (2006.01) |

(52) U.S. Cl.
CPC ............. *G01N 33/49* (2013.01); *G01N 33/48* (2013.01); *G01N 33/88* (2013.01); *G01N 2333/4737* (2013.01); *G01N 2800/304* (2013.01)

(58) Field of Classification Search
CPC ...................................................... G01N 33/53
See application file for complete search history.

(56) References Cited

FOREIGN PATENT DOCUMENTS

WO    WO 2013/009183 A1    1/2013

OTHER PUBLICATIONS

Dunlop et al, Mental Health in Family Medicine, 2013; 10: 175-81 (Year: 2013).*
Ma et al., Cardiology Research and Practice, vol. 2011, Article ID 286509, p. 1-8 (Year: 2011).*
International Search Report and Written Opinion, PCT/CA2016/050036, dated Apr. 20, 2016.
Felger, J.C. et al., "Inflammatory Cytokines in Depression: Neurobiological Mechanisms and Therapeutic Implications," Neuroscience 246 (2013), pp. 199-229.
Setiawan, E. PhD. et al., "Role of Translocator Protein Density, a Marker of Neuroinflammation, in the Brain During Major Depressive Episodes," JAMA Psychiatry 72 (3) (2015), pp. 268-275.

* cited by examiner

*Primary Examiner* — Ruth A Davis
(74) *Attorney, Agent, or Firm* — Winston & Strawn LLP

(57) ABSTRACT

Provided are methods for determining the level of microglial activation in the brain of a subject by measuring blood Prostaglandin E2 (PGE2), Prostaglandin F2α, or both, and C-Reactive Protein (CRP) concentrations in a sample obtained from a subject, wherein the ratio of [PGE2]/[CRP], [PGF2α]/[CRP], or both, is indicative of the level of microglial activation in the brain of the subject.

8 Claims, 14 Drawing Sheets

PERIPHERAL MEASURE OF CENTRAL BRAIN INFLAMMATION, MARKERS THEREFOR AND USES THEREOF

This application is a 371 filing of international Patent Application PCT/CA2016/050036 filed Jan. 15, 2016, which claims the benefit of U.S. application No. 62/103,773 filed Jan. 15, 2015.

FIELD OF INVENTION

The present invention relates to peripheral measures of central brain inflammation, markers therefor and uses thereof.

BACKGROUND OF THE INVENTION

Major depressive disorder (MDD) is highly prevalent and impactful, with active symptoms present in 4% of the adult population (1). Although MDD exhibits multiple molecular phenotypes (2-5) there is accumulating evidence for a role of inflammation in generating symptoms of a major depressive episode (MDE). For example, induction of inflammation is associated with sad mood in humans (6) and direct induction of the central immune system in rodents is associated with the sickness syndrome of anhedonia, weight loss and anorexia which overlap with the diagnostic criteria for MDE (7). Also in MDD, several markers of peripheral inflammation, including C-reactive protein, IL-6 and TNF-$\alpha$ are frequently increased (8). Interestingly, conditions which create neuroinflammation such as traumatic brain injury, systemic lupus erythematosus and multiple sclerosis are associated with prevalence rates of MDE as high as 50% suggesting a link between brain inflammation and mood symptoms (9).

Obsessive compulsive disorder (OCD) is another prevalent disorder which affects many. OCD is an example of a neuropsychiatric disorder which may be associated with, or diagnosed along with, MDD. The exact cause of OCD remains unclear, and diagnosis is most often based on the symptoms experienced and the severity thereof.

Presently, it is not clear whether brain inflammation occurs during a current major depressive episode (MDE) because most postmortem investigations of neuroinflammation sampled either MDD with a history of MDE or suicide victims with varied diagnoses. Within such studies, the samples of subjects with current MDE were small. Van Otterloo et al., (10) reported no difference in density of activated microglia, in the white matter of the orbitofrontal region in 10 MDD subjects. Dean et al. sampled 10 MDD subjects and found significantly increased levels of the transmembrane form of TNF in the dorsolateral prefrontal cortex but no difference in levels of this form of TNF in the anterior cingulate cortex and no difference in the soluble form of TNF in either region (11). Steiner et al. reported increased density of quinolinic acid positive cells, a marker influenced by microglial activation, in the anterior cingulate cortex of 7 MDE subjects (12). Microarray studies have had mixed results, with a positive finding by Shelton et al. of increased pro- and anti-inflammatory cytokine mRNA in Brodmann Area 10 (BA10) in 14 MDD subjects (13) but several other microarray studies, most of which sampled adjacent regions of the prefrontal cortex, did not identify this result (14, 15) Amongst investigations in suicide victims one study reported greater HLA-DR staining, a marker of microglial activation, in the dorsolateral prefrontal and anterior cingulate cortex (16) and a second study reported greater levels of IL-6, TNF-$\alpha$, and IL-1$\beta$ in BA10 (17). Neither study of suicide found a relationship to MDD (or MDE) but there were less than 10 subjects with MDD in each study. The mixed results among postmortem investigations in MDD have been attributed to issues of variation in brain regions sampled, inclusion of early and late onset MDD, comorbidity of other psychiatric disorders and addiction and, with the exception of the microarray studies, small sample size, although it is plausible that lack of focus on sampling the state of MDE may be important for investigations of neuroinflammation. Torres-Platas reported an increased ratio of primed relative to ramified microglia in the white matter of the dorsal anterior cingulated white matter in a sample of 24 depressed suicide victims compared to 17 healthy controls, however, this was one of three ratios evaluated so it is unclear whether this result would be statistically meaningful if corrected for by the number of comparisons completed.

To determine whether neuroinflammation occurs in MDE secondary to MDD, positron emission tomography may be applied to measure translocator protein (TSPO) binding in vivo. TSPO is an 18 kDa protein located on outer mitochondrial membranes in microglia and increased expression of TSPO occurs when microglia are activated during neuroinflammation (18). Recently, a new generation of positron emission tomography (PET) radiotracers were developed with superior quantification of TSPO binding and among these, [18F]FEPPA has excellent properties including high, selective affinity for TSPO (19), increased binding during induced neuroinflammation (20) and a high ratio of specific binding relative to free and non-specific binding (21).

To date, one neuroimaging study applied [11C]PBR28 PET to investigate TSPO levels in MDD, which was negative (22). This earlier study assessed whether TSPO levels were elevated in a sample of 10 MDD subjects (scanned once) under a variety of states (treated, untreated, symptomatic, partially symptomatic) hence, this study cannot be considered definitive for determining whether TSPO binding is elevated in MDE. Scores on the Montgomery-Asberg Depression Rating Scale on the PET scan day ranged from 5 to 30, indicating that the severity ranged from almost asymptomatic to moderately symptomatic. Other issues which limit interpretation of this study include potential bias of ongoing antidepressant use, heterogeneity of combined sampling of early and late onset MDD, and incomplete information regarding a TSPO polymorphism (rs6971) known to influence binding of the new generation of TSPO PET radioligands, including [11C]PBR28 and [18F]FEPPA (23, 24).

Since imaging the brain during a MDE is costly, technically challenging and impractical in a clinical setting, peripheral markers correlating to brain inflammation, depression, MDE, MDD, and/or other neuropsychiatric disorders such as, for example, OCD, are needed. Further, there is also a need in the art for peripheral measures correlating to microglia activation in a subject.

SUMMARY OF INVENTION

In an embodiment, there is provided herein a method for determining the level of microglial activation in the brain of a subject comprising measuring blood Prostaglandin E2 (PGE2), blood Prostaglandin F2$\alpha$, or both, and C-Reactive Protein (CRP) concentrations in a sample obtained from a subject, wherein the ratio of blood [PGE2]/[CRP], the ratio of blood [PGF2$\alpha$]/[CRP], or both, is indicative of the level of microglial activation in the brain of the subject.

In an embodiment, there is provided herein a method for determining the level of microglial activation in the brain of a subject comprising measuring blood Prostaglandin E2 (PGE2) and C-Reactive Protein (CRP) concentrations in a sample obtained from a subject, wherein the ratio of blood [PGE2]/[CRP] is indicative of the level of microglial activation in the brain of the subject.

In an embodiment, there is provided herein a method for determining the level of microglial activation in the brain of a subject comprising measuring blood Prostaglandin F2α, and C-Reactive Protein (CRP) concentrations in a sample obtained from a subject, wherein the ratio of blood [PGF2α]/[CRP] is indicative of the level of microglial activation in the brain of the subject.

In another embodiment of a method as described above, the method may further comprise a step of recommending a treatment option for the subject based on the level of microglial activation in the brain.

In yet another embodiment of any of the method or methods as described above, the sample may be a blood sample, and PGE2, PGF2α, or both PGE2 and PGF2α, and CRP may be measured from blood or plasma in the sample. Preferably, the sample may be a serum sample, and PGE2, PGF2α, or both PGE2 and PGF2α, and CRP may be measured in the serum sample.

In still another embodiment of any of the method or methods as described above, the subject may be clinically depressed, suspected of being clinically depressed or has exhibited one or more symptoms of depression, or one or more other neuropsychiatric illnesses.

In yet another embodiment of any of the method or methods as described above, the subject may be diagnosed or suspected of having major depressive episode (MDE) or major depressive disorder (MDD).

In still another embodiment of any of the method or methods as described above, the subject may exhibit major depressive episode (MDE) secondary to major depressive disorder (MDD).

In still another embodiment of any of the method or methods as described above, the subject may have obsessive compulsive disorder (OCD), may be suspected of having OCD, or may have exhibited one or more symptoms of OCD, and the ratio of blood [PGE2]/[CRP] may be used as indicative of the level of microglial activation in the brain of the subject.

In another embodiment of any of the method or methods as described above, the PGE2, PGF2α, or both, and CRP may be quantified by mass spectrometry, HPLC, immunoassay, radioimmunoassay, gas chromatography-mass spectrometry or other chromatographic or non-chromatographic procedure.

In yet another embodiment of any of the method or methods as described above, the method may further comprise obtaining a blood or serum sample from the subject.

In another embodiment of any of the method or methods as described above, the microglial activation may be in the prefrontal cortex, insula or any other region of the brain.

In still another embodiment of any of the method or methods as described above, said subject may exhibit MDE, MDD or depression as determined by the Structures Clinical Interview for DSM-V, Hamilton Depression rating Scale or another psychiatric rating scale.

In another embodiment of any of the method or methods as described above, said method may further comprise determining the level of microglial activation in the brain of one or more other subject(s) or group of subjects, for example one or more other subjects or groups of subjects having depression, OCD, another neuropsychiatric illness, or healthy subjects, at a single time point or over multiple timepoints, comprising measuring blood Prostaglandin E2 (PGE2), PGF2α, or both, and C-Reactive Protein (CRP) concentrations in a sample obtained from the one or more other subject(s) or group of subjects, for example one or more other subjects or groups of subjects having depression, OCD, another neuropsychiatric illness, or healthy subjects, at a single time point or over multiple timepoints, wherein the ratio of [PGE2]/[CRP], [PGF2α]/[CRP], or both, is indicative of the level of microglial activation in the brain of the one or more other subject(s) or group of subjects, for example one or more other subjects or groups of subjects having depression, OCD, another neuropsychiatric illness, or healthy subjects, at a single time point or over multiple timepoints.

In still another embodiment of any of the method or methods as described above, the ratio of blood [PGE2]/[CRP], blood [PGF2α]/[CRP], or both, of the subject may be compared to the ratio of blood [PGE2]/[CRP], [PGF2α]/[CRP], or both, of the one or more other subject or group of subjects, for example one or more other subjects or groups of subjects having depression, OCD, another neuropsychiatric illness, or healthy subjects, at a single time point or over multiple timepoints.

In still another embodiment of any of the method or methods as described above, a higher ratio of blood [PGE2]/[CRP], [PGF2α]/[CRP], or both for the subject compared to blood [PGE2]/[CRP], [PGF2α]/[CRP], or both of the one or more other subject(s) or group of subjects, for example one or more other subjects or groups of subjects having depression, OCD, another neuropsychiatric illness, or healthy subjects, at a single time point or over multiple timepoints, may indicate a greater level of microglial activation in the brain of the subject.

In still another embodiment of any method or methods as described above, a higher ratio of blood [PGE2]/[CRP], [PGF2α]/[CRP], or both for the subject compared to blood [PGE2]/[CRP], [PGF2α]/[CRP], or both the same subject as determined at a previous timepoint may indicate a greater level of microglial activation in the brain of the subject as compared to the level of microglial activation in the brain of the subject at the previous timepoint.

In still another embodiment of any method or methods as described above, a lower ratio of blood [PGE2]/[CRP], [PGF2α]/[CRP], or both for the subject compared to blood [PGE2]/[CRP], [PGF2α]/[CRP], or both the same subject as determined at a previous timepoint may indicate a lower level of microglial activation in the brain of the subject as compared to the level of microglial activation in the brain of the subject at the previous timepoint.

In still another embodiment of any of the method or methods as described above, the level of microglial activation may be an index of brain inflammation.

In still another embodiment of any of the method or methods as described above, the greater level of microglial activation may be an indication of an greater amount of brain inflammation in the subject compared to the one or more other subject(s) or group of subjects, for example one or more other subjects or groups of subjects having depression, OCD, another neuropsychiatric illness, or healthy subjects, at a single time point or over multiple timepoints, or as compared to the amount of brain inflammation in the subject at another timepoint.

In another embodiment of any of the method or methods as described above, the level of microglial activation may identify, or assist in identifying, the subject as having depression, a major depressive episode (MDE), a major depressive disorder (MDD), obsessive compulsive disorder (OCD), or other neuropsychiatric illness, or prone to developing depression, MDE, MDD, OCD, or other neuropsychiatric illness, or as having brain inflammation concurrent with depression, a major depressive episode (MDE), a major depressive disorder (MDD), obsessive compulsive disorder (OCD), or other neuropsychiatric illness.

In another embodiment of any of the method or methods as described above, the ratio of blood [PGE2]/[CRP] may be used as indicative of the level of microglial activation in the brain of the subject.

In another embodiment of any of the method or methods as described above, the ratio of blood [PGF2α]/[CRP] may be used as indicative of the level of microglial activation in the brain of the subject.

In another embodiment of any of the method or methods as described above, both the ratio of blood [PGE2]/[CRP] and [PGF2α]/[CRP] may be used as indicative of the level of microglial activation in the brain of the subject.

In yet another embodiment of any of the method or methods as described above, the greater level of microglial activation may identify, or assist in identifying, the subject as having depression, a major depressive episode (MDE), a major depressive disorder (MDD), OCD, or other neuropsychiatric illness or prone to developing depression, MDE, MDD, OCD, or other neuropsychiatric illness, or as having brain inflammation concurrent with depression, a major depressive episode (MDE), a major depressive disorder (MDD), obsessive compulsive disorder (OCD), or other neuropsychiatric illness, as compared to the one or more other subjects or groups of subjects having depression, OCD, another neuropsychiatric illness, or healthy subjects, at a single time point or over multiple timepoints.

In another embodiment, there is provided herein a method for determining susceptibility, or assisting in determining susceptibility, to a depressive disorder in a subject, said method comprising the steps of: a) detecting and determining blood PGE2 concentration, blood PGF2α concentration, or both, and CRP concentration, and determining the ratio of [PGE2]/[CRP], [PGF2α]/[CRP], or both, or log or natural log transformation of [PGE2]/[CRP], [PGF2α]/[CRP], or both, in said blood sample; b) correlating the ratio of [PGE2]/[CRP], [PGF2α]/[CRP], or both, or log or natural log transformation of [PGE2]/[CRP], [PGF2α]/[CRP], or both, in said blood sample to a control group having depression, another neuropsychiatric illness, or healthy subjects, at a single time point or over multiple timepoints, in order to determine susceptibility to depressive disorder in the subject.

In another embodiment, there is provided herein a method for determining susceptibility, or assisting in determining susceptibility, to a depressive disorder in a subject, said method comprising the steps of: a) detecting and determining blood PGE2 concentration and CRP concentration, and determining the ratio of [PGE2]/[CRP] or log or natural log transformation of [PGE2]/[CRP] in said blood sample; b) correlating the ratio of [PGE2]/[CRP], or log or natural log transformation of [PGE2]/[CRP] in said blood sample to a control group having depression, another neuropsychiatric illness, or healthy subjects, at a single time point or over multiple timepoints, in order to determine susceptibility to depressive disorder in the subject.

In another embodiment, there is provided herein a method for determining susceptibility, or assisting in determining susceptibility, to a depressive disorder in a subject, said method comprising the steps of: a) detecting and determining blood PGF2α concentration and CRP concentration, and determining the ratio of [PGF2α]/[CRP] or log or natural log transformation of [PGF2α]/[CRP] in said blood sample; b) correlating the ratio of [PGF2α]/[CRP], or log or natural log transformation of [PGF2α]/[CRP] in said blood sample to a control group having depression, another neuropsychiatric illness, or healthy subjects, at a single time point or over multiple timepoints, in order to determine susceptibility to depressive disorder in the subject.

In another embodiment, there is provided herein a method for determining susceptibility, or assisting in determining susceptibility, to an obsessive compulsive disorder in a subject, said method comprising the steps of: a) detecting and determining blood PGE2 concentration and CRP concentration, and determining the ratio of [PGE2]/[CRP] or log or natural log transformation of [PGE2]/[CRP] in said blood sample; b) correlating the ratio of [PGE2]/[CRP], or log or natural log transformation of [PGE2]/[CRP] in said blood sample to a control group having OCD, another neuropsychiatric illness, or healthy subjects, at a single time point or over multiple timepoints, in order to determine susceptibility to obsessive compulsive disorder in the subject.

In yet another embodiment of any of the method or methods as described above, the method may further comprise treating the subject with medication, non-medicinal therapy or a combination thereof; monitoring the subject; counseling the subject; testing or screening the subject for clinical depression, major depressive episode, major depressive disorder, OCD, or any other neuropsychiatric illness, testing the blood sample for one or more additional genetic markers, nucleotide sequences, proteins, metabolites or any combination thereof.

In yet another embodiment of any of the method or methods as described above, treating the subject with medication may comprise administering one or more anti-inflammatory agents, antidepressants, antipsychotics, mood stabilizers, anticonvulsants, antianxiolytics, steroids, or any combination thereof.

In yet another embodiment of any of the method or methods as described above, the medication may comprise one or more antidepressants, anti-inflammatory agents, antipsychotics, mood stabilizers, anticonvulsants, antianxiolytics, or any combination thereof such as glucocorticoids, phosphodiesterase inhibitors, cox-2 inhibitors, acetaminophen, non-steroidal anti-inflammatory agents, statins, neurokinin antagonists, thiazolidinediones, toll receptor antagonists/agonists, tetracycline antibiotics such as, but not limited to minocycline, cytokine antagonists such as, but not limited to infliximab, P2X7 receptor binding medications, riluzole, Janus kinase inhibitors, phospholipase inhibitors, antibody directed therapies for immune system targets, Monoamime Oxidase Inhibitor (MAOIs) such as, but not limited to, tranylcypromine, phenelzine, isocarboxazid and the like, Tricyclic Antidepressants (TCAs) such as, but not limited to clomipramine, amitriptyline, desipramine, nortriptyline, doxepin, or trimipramine, Selective Serotonin Reuptake Inhibitors (SSRIs) such as, but not limited to citalopram, escitalopram, fluvoxamine, paroxetine, fluoxetine, sertraline or other common medications such as, but not limited to duloxetine, venlafaxine, mirtazapine, bupropion, trazodone, clozapine, lithium, ketamine any pharmaceutically acceptable salt or derivative thereof or any combination thereof.

In still another embodiment, there is provided herein a method of measuring microglial activation in the brain of a subject in response to treatment comprising the steps of measuring blood Prostaglandin E2 (PGE2), Prostaglandin F2α, or both, and C-Reactive Protein (CRP) concentrations from a first blood sample obtained from the subject at a first time and a second blood sample obtained from the same subject after or during treatment, wherein a decrease in the ratio of blood [PGE2]/[CRP], [PGF2α]/[CRP], or both in the first sample compared to the second sample may be indicative of reduced microglial activation in the brain after or during treatment.

In yet another embodiment of any of the method or methods as described above, the treatment may comprise drug treatment.

In yet another embodiment of any of the method or methods as described above, the blood sample may be a serum sample.

In still another embodiment of any of the method or methods as described above, the drug treatment may comprise anti-inflammatory or immunomodulator drug treatment.

In another embodiment of any of the method or methods as described above, the subject may be clinically depressed, suspected of being clinically depressed, or may have exhibited one or more symptoms of depression, or one or more other neuropsychiatric illnesses.

In another embodiment of any of the method or methods as described above, the subject may have OCD, be suspected of having OCD, or may have exhibited one or more symptoms of OCD.

In another embodiment of any of the method or methods as described above, the level of microglial activation may be an index of brain inflammation.

In still another embodiment, there is provided herein a method of reducing microglial activation in the brain of a subject comprising administering to said subject an anti-inflammatory agent to reduce microglial activation in the subject.

In another embodiment of any of the method or methods as described above, the method may reduce brain inflammation as a result of reducing microglial activation.

In yet another embodiment of any of the method or methods as described above, the method may treat a subject exhibiting or having a propensity to develop depression, major depressive episode (MDE), major depressive disorder (MDD), OCD, or other neuropsychiatric illness.

In another embodiment of any of the method or methods as described above, the subject may be further subjected to brain imaging.

In another embodiment, there is provided herein a kit comprising one or more markers of microglial activation, one or more markers of brain inflammation, one or more markers of peripheral body inflammation, one or more diagnostic agents capable of quantifying or assisting in quantifying one or more markers of microglial activation, one or more markers of brain inflammation, one or more markers of peripheral body inflammation or any combination thereof.

In another embodiment of the kit as described above, the one or more diagnostic agents may comprise one or more antibodies or antibody derivatives or an agent, component, diluent, or buffer which may be employed in mass spectrometry, HPLC, immunoassay, radioimmunoassay, gas chromatography-mass spectrometry or other chromatographic or non-chromatographic procedure to quantify the one or more markers.

In yet another embodiment of any of the kit or kits as described above, the kit may comprise an antibody or other agent specific for detecting or quantifying one or more of PGE2, PGF2α, or CRP in a blood sample.

In another embodiment, there is provided herein a method for identifying candidates for treating brain inflammation in a subject having a neuropsychiatric illness, said method comprising: (a) measuring blood Prostaglandin E2 (PGE2), blood Prostaglandin F2α, or both, and C-Reactive Protein (CRP) pre-treatment concentrations in a pre-treatment sample obtained from the subject prior to administration of a potential agent for treating brain inflammation; (b) administering the potential agent for treating brain inflammation; and (c) measuring blood Prostaglandin E2 (PGE2), blood Prostaglandin F2α, or both, and C-Reactive Protein (CRP) post-treatment concentrations in a post-treatment sample obtained from the subject following administration of the potential agent for treating brain inflammation; wherein a reduction in [PGE2]/[CRP], [PGF2α]/[CRP], or both, post-treatment indicates that the potential agent is a candidate for treating brain inflammation in a subject having a neuropsychiatric illness.

BRIEF DESCRIPTION OF THE DRAWINGS

These and other features of the invention will become more apparent from the following description in which reference is made to the appended drawings wherein.

DETAILED DESCRIPTION

Figure 1:
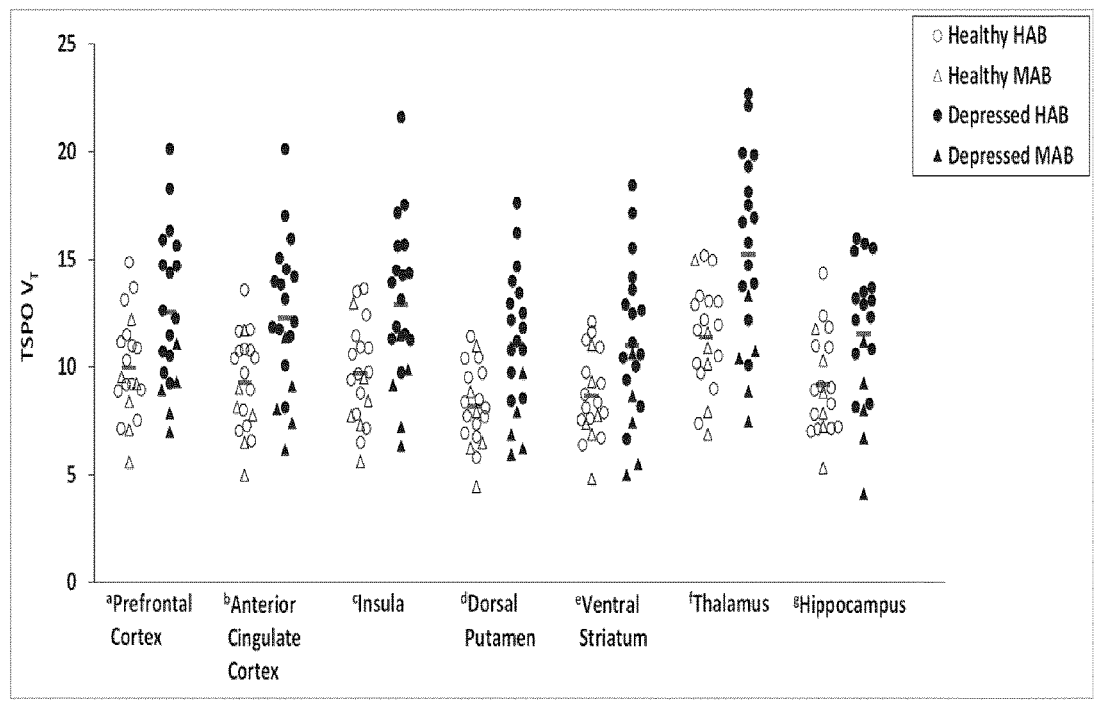
FIG. 1 shows elevated translocator protein density (TSPO VT) during a major depressive episode (MDE) secondary to major depressive disorder (MDD). TSPO VT was significantly greater in MDE of MDD (Depressed, N=20, 15 HAB, 5 MAB) compared to controls (Healthy, N=20, 14 HAB, 6 MAB): ANOVAs, aprefrontal cortex, $F_{1,37}=8.07$, $P=0.007$; banterior cingulate cortex, $F_{1,37}=12.24$, $P=0.001$; cinsula, $F_{1,37}=12.34$, $P=0.001$; ddorsal putamen, $F_{1,37}=14.1$, $P=0.001$; eventral striatum, $F_{1,37}=6.9$, $P=0.013$; fthalamus, $F_{1,37}=13.6$, $P=0.001$; ghippocampus, $F_{1,37}=7.5$, $P=0.009$. All second generation TSPO radioligands, such as [18F]FEPPA, show differential binding according to the SNP rs6971 of the TSPO gene resulting in high affinity binders (HAB) and mixed affinity binders (MAB). Bars indicate means in each group.

The following description is of preferred embodiments.

The present invention relates to peripheral measures of central brain inflammation, markers therefor and uses thereof. In a further aspect, the present invention relates to diagnostic and prognostic markers for depressive disorders or OCD. The present invention also relates to identifying subjects that have increased ratio of blood and/or plasma concentration of [PGE2]/[CRP], [PGF2α]/[CRP], or both, compared to a control group, for example a control group that does not have a depressive disorder, a control group having a depressive disorder, or a control group having a neuropsychiatric disorder. The present invention also relates to identifying whether a subject's ratio of blood, serum, and/or plasma concentration of [PGE2]/[CRP], [PGF2α]/[CRP], or both, have increased compared to a previous time point (i.e. monitoring changes over time). The present invention further relates to methods of measuring brain inflammation, markers useful as indicators of brain inflammation and uses of markers to diagnose subjects or to test and identify medicines which may be useful to reduce brain inflammation and/or treat depressive disorders and/or OCD and/or symptoms associated therewith.

In an embodiment of the instant application there is provided a method for determining the level of microglial activation in the brain of a subject comprising measuring blood Prostaglandin E2 (PGE2) and C-Reactive Protein (CRP) concentrations in a sample obtained from a subject, wherein the ratio of [PGE2]/[CRP] is indicative of the level of microglial activation in the brain of the subject.

In another embodiment of the instant application there is provided a method for determining the level of microglial activation in the brain of a subject comprising measuring blood Prostaglandin F2α (PGF2α) and C-Reactive Protein (CRP) concentrations in a sample obtained from a subject, wherein the ratio of [PGF2α]/[CRP] is indicative of the level of microglial activation in the brain of the subject.

In yet another embodiment of the instant application there is provided a method for determining the level of microglial activation in the brain of a subject comprising measuring both blood Prostaglandin E2 (PGE2) and blood Prostaglandin F2α (PGF2α), and C-Reactive Protein (CRP) concentrations in a sample obtained from a subject, wherein the ratio of [PGE2]/[CRP] and [PGF2α]/[CRP] is indicative of the level of microglial activation in the brain of the subject.

In still another embodiment, a method as described above may further comprising performing additional suitable conventional diagnosis steps, such as those described in DSM-V.

In still another embodiment, any of the method or methods as described above may further comprise a step of recommending a treatment option for the subject based on the level of microglial activation in the brain. For example, a subject determined as having an elevated level of [PGE2]/[CRP], [PGF2α]/[CRP], or both, may be recommended a treatment program involving treatment to reduce brain inflammation using, for example, treatments described in further detail below. Where a subject is afflicted with a neuropsychiatric illness related to elevated brain inflammation, the subject may be recommended a treatment program involving a conventional treatment for the neuropsychiatric illness alone, or in combination with a treatment for reducing or controlling brain inflammation.

It will be understood that in certain embodiments, [PGE2], [PGF2α], and [CRP] may be measured in a blood sample obtained from a subject, or in a plasma or serum sample obtained therefrom. Preferably, [PGE2], [PGF2α], and [CRP] may be measured in a peripheral blood sample such as a serum sample.

The person of skill in the art having regard to the teachings herein will understand that brain inflammation levels may be correlated with [PGE2]/[CRP], [PGF2α]/[CRP], or both. Determining a threshold level of [PGE2]/[CRP], [PGF2α]/[CRP], or both, beyond which brain inflammation levels in a subject may be considered as being elevated may vary between different subject populations or different applications. Generally, a [PGE2]/[CRP] value, measured in peripheral blood (i.e. serum), which is above a healthy subject's [PGE2]/[CRP] value, or the same subject's [PGE2]/[CRP] value at a prior time point, determined in the same manner, may be considered as being elevated. Generally, a [PGF2α]/[CRP] value, measured in peripheral blood, which is above a healthy subject's [PGF2α]/[CRP] value, or the same subject's [PGE2]/[CRP] value at a prior time point, determined in the same manner, may be considered as being elevated.

It will be understood by the person of skill in the art having regard to the teachings herein that brain inflammation levels may be correlated with [PGE2]/[CRP], [PGF2α]/[CRP], or both. Thus, it is contemplated herein that any of the method or methods described herein may involve monitoring or determining [PGE2]/[CRP], [PGF2α]/[CRP], or both, over time to determine whether a subject's level of microglial activation, or brain inflammation, has increased or decreased over the period of time. By way of example, determination of an increase in [PGE2]/[CRP], [PGF2α]/[CRP], or both, from an initial time point to a subsequent time point may suggest that an increase in microglial activation, or brain inflammation, has occurred over the intervening time period, or that microglial activation and/or brain inflammation is higher at the subsequent time point than it was at the initial time point. Monitoring or determining [PGE2]/[CRP], [PGF2α]/[CRP], or both, of a subject, such as a subject having MDD, MDE, depression, or OCD, over time may assist in determining whether microglial activation and/or brain inflammation is improving or worsening either naturally or in response to a treatment program.

As shown herein, brain inflammation may be present during MDE, and associated with depression conditions. Thus, an elevated level of microglial activation as determined according to methods described herein may identify, or assist in identifying, a subject as having or being prone to develop a neuropsychiatric illness such as but not limited to MDE, MDD, depression, or OCD, or any combination thereof.

In another embodiment, a method for determining microglial activation in a subject may identify, or assist in identifying, whether a subject having a neuropsychiatric illness such as but not limited to MDE, MDD, depression, or OCD, has brain inflammation.

The present invention also provides a method for diagnosing, or assisting in diagnosing, a subject as having depressive disorder or susceptibility to a depressive disorder from a blood sample taken from a subject, the method comprising the steps of:

a) detecting and determining blood PGE2 concentration, blood PGF2α concentration, or both, and CRP concentration, and determining the ratio of [PGE2]/[CRP], [PGF2α]/[CRP], or both, in said blood sample, and;

b) correlating the ratio of blood [PGE2]/[CRP], [PGF2α]/[CRP], or both, in said blood sample to a control group having depression, another neuropsychiatric illness, or healthy subjects, at a single time point or over multiple timepoints, in order to diagnose depressive disorder or susceptibility to the depressive disorder in the subject.

The present invention also provides a method for diagnosing, or assisting in diagnosing, a subject as having OCD or susceptibility to OCD from a blood sample taken from a subject, the method comprising the steps of:

a) detecting and determining blood PGE2 concentration and CRP concentration, and determining the ratio of [PGE2]/[CRP] in said blood sample, and;

b) correlating the ratio of blood [PGE2]/[CRP] in said blood sample to a control group having OCD, another neuropsychiatric illness, or healthy subjects, at a single time point or over multiple timepoints, in order to diagnose OCD or susceptibility to OCD in the subject.

The present invention also provides a method for diagnosing, or assisting in diagnosing, a subject as having depressive disorder or susceptibility to a depressive disorder from a blood sample taken from a subject, the method comprising the steps of:

a) detecting and determining blood PGE2 concentration and CRP concentration and determining the ratio of [PGE2]/[CRP] in said blood sample, and;

b) correlating the ratio of blood [PGE2]/[CRP] in said blood sample to a control group having depression, another neuropsychiatric illness, or healthy subjects, at a single time point or over multiple timepoints, in order to diagnose depressive disorder or susceptibility to the depressive disorder in the subject.

The present invention also provides a method for diagnosing, or assisting in diagnosing, a subject as having depressive disorder or susceptibility to a depressive disorder from a blood sample taken from a subject, the method comprising the steps of:

a) detecting and determining blood PGF2α concentration and CRP concentration and determining the ratio of [PGF2α]/[CRP] in said blood sample, and;

b) correlating the ratio of blood [PGF2α]/[CRP] in said blood sample to a control group having depression, another neuropsychiatric illness, or healthy subjects, at a single time point or over multiple timepoints, in order to diagnose depressive disorder or susceptibility to the depressive disorder in the subject.

In an embodiment, both blood [PGE2]/[CRP] and [PGF2α]/[CRP] may be determined and correlated to a control group which has a depressive disorder, or to a healthy control group, in order to diagnose, or assist in diagnosing, depressive disorder or susceptibility to the depressive disorder in the subject.

In a further embodiment there is provided a method of measuring microglial activation in the brain of a subject in response to treatment comprising the steps of measuring blood Prostaglandin E2 (PGE2), PGF2α, or both, and C-Reactive Protein (CRP) concentrations from a first blood sample obtained from the subject at a first time and a second blood sample obtained from the same subject after or during treatment, wherein a decrease in the ratio of blood [PGE2]/[CRP], [PGF2α]/[CRP], or both, in the first sample compared to the second sample is indicative of reduced microglial activation in the brain after or during treatment.

The samples obtained from the subject are blood samples and PGE2, PGF2α, or both, and CRP are typically measured and quantified from blood using standard procedures known in the art. The methodologies used to identify and quantify PGE2, PGF2α, or both and CRP are not meant to be limiting in any manner. Representative examples of methodologies which may be employed to quantify PGE2, PGF2α, or both, and CRP include, but are not limited to mass spectrometry, HPLC, immunoassay, radioimmunoassay, gas chromatography-mass spectrometry or other chromatographic or non-chromatographic procedures.

In a preferred embodiment, but without wishing to be considered limiting, a specific ratio of [PGE2]/[CRP] may be used to determine if a subject may have or be more likely to develop a depressive disorder or other neuropsychiatric disorder, for example a brain disorder or general medical illness with disease in the brain associated with symptoms that may be treated by the branches of medicine that include psychiatry or neurology. For example, but not wishing to be limiting, a [PGE2]/[CRP] value greater than 250 may be used, for example between 250 and 100000 or any individual unit within this range, including, but not limited to 250, 260, 270, 280, 290, 300, 310, 320, 330, 340, 350, 355, 360, 365, 370, 375, 380, 390, 400, 410, 420, 430, 440, 450, 460, 470, 480, 490, 500, 510, 520, 530, 540, 550, 560, 570, 580, 590, 600, 700, 800, 900, 1000, 2000, 3000, 4000, 5000, 6000, 7000, 8000, 9000, 10000, 20000, 30000, 40000, 50000 or more. These values are meant to representative and should not be limited within the full range provided above. Also, in the methods described herein it is also contemplated that ratio of [CRP]/[PGE2] may be employed as it is the inverse of the ratio of [PGE2]/[CRP]. Similarly it is also contemplated that the log or natural log (ln) of [PGE2]/[CRP], log or natural log (ln) [CRP]/[PGE2] or other mathematical transformation may be employed in any of the methods described herein.

In a preferred embodiment, but without wishing to be considered limiting, a specific ratio of [PGF2α]/[CRP] may be used to determine if a subject may have or be more likely to develop a depressive disorder or other neuropsychiatric disorder, for example a brain disorder or general medical illness with disease in the brain associated with symptoms that may be treated by the branches of medicine that include psychiatry or neurology. For example, but not wishing to be limiting, a [PGF2α]/[CRP] value greater than 50 may be used, for example between 50 and 100000 or any individual unit within this range, including, but not limited to 50, 60, 70, 80, 90, 100, 110, 120, 130, 140, 150, 160, 170, 180, 190, 200, 220, 225, 230, 240, 250, 260, 270, 275, 300, 310, 320, 323, 325, 330, 340, 350, 375, 380, 390, 400, 410, 420, 430, 440, 450, 460, 470, 480, 490, 500, 510, 520, 530, 540, 550, 560, 570, 580, 590, 600, 700, 800, 900, 1000, 2000, 3000, 4000, 5000, 6000, 7000, 8000, 9000, 10000, 20000, 30000, 40000, 50000 or more. In an embodiment, preferably, a [PGF2α]/[CRP] value of about 100 or greater than about 100 may be used. These values are meant to representative and should not be limited within the full range provided above. Also, in the methods described herein it is also contemplated that ratio of [CRP]/[PGF2α] may be employed as it is the inverse of the ratio of [PGF2α]/[CRP]. Similarly it is also contemplated that the log or natural log (ln) of [PGF2α]/[CRP], log or natural log (ln) [CRP]/[PGF2α] or other mathematical transformation may be employed in any of the methods described herein.

In a preferred embodiment, but without wishing to be considered limiting, a specific ratio of [PGE2]/[CRP] may be used to determine if a subject may have or be more likely to develop OCD or other neuropsychiatric disorder, for example a brain disorder or general medical illness with disease in the brain associated with symptoms that may be treated by the branches of medicine that include psychiatry or neurology. For example, but not wishing to be limiting, a [PGE2]/[CRP] value greater than 250 may be used, for example between 250 and 100000 or any individual unit within this range, including, but not limited to 250, 260, 270, 280, 290, 300, 310, 320, 330, 340, 350, 355, 360, 365, 370, 375, 380, 390, 400, 410, 420, 430, 440, 450, 460, 470, 480, 490, 500, 510, 520, 530, 540, 550, 560, 570, 580, 590, 600, 700, 800, 900, 1000, 2000, 3000, 4000, 5000, 6000, 7000, 8000, 9000, 10000, 20000, 30000, 40000, 50000 or more. In an embodiment, preferably, a [PGE2]/[CRP] value of about 500 or greater than about 500 may be used. These values are meant to representative and should not be limited within the full range provided above. Also, in the methods described herein it is also contemplated that ratio of [CRP]/[PGE2] may be employed as it is the inverse of the ratio of [PGE2]/[CRP]. Similarly it is also contemplated that the log or natural log (ln) of [PGE2]/[CRP], log or natural log (ln) [CRP]/[PGE2] or other mathematical transformation may be employed in any of the methods described herein.

In methods described above, it is contemplated that a subject may be clinically depressed, suspected of being clinically depressed or has exhibited one or more symptoms of depression, or one or more other neuropsychiatric illnesses. For example, but not wishing to be considered limiting in any manner, the subject may be diagnosed or suspected of having major depressive episode (MDE) or major depressive disorder (MDD). MDD can be further subcategorized as being atypical depression, melancholic depression, psychotic major depression, catatonic depression, postpartum depression and seasonal affective disorder. Depressive disorders may further comprise dysthymia and depressive disorder not otherwise specified and bipolar disorder (or manic-depression). Depressive disorders not otherwise specified include recurrent brief depression and minor depressive disorder. Bipolar disorder is a neuropsychiatric illness that can also be subcategorized into bipolar I, bipolar II, cyclothymia and bipolar disorder not otherwise specified. In a further embodiment, the subject may exhibit major depressive episode (MDE) secondary to major depressive disorder (MDD). Preferably, depression, MDE, MDD or one or more neuropsychiatric illnesses is diagnosed in a subject or patient according to the Structures Clinical Interview for DSM-V, Hamilton Depression rating Scale or another psychiatric rating scale. However, it is also contemplated that the methods as described herein may be practiced in subjects or patients who are suspected of having depression or a depressive disorder without a formal diagnosis. In still a further embodiment, the subject may have no symptoms of any illness.

In a further embodiment the methods described herein further comprise determining the level of microglial activation in the brain of one or more other subject(s) or group of subjects, for example one or more other subjects or groups of subjects having depression, OCD, another neuropsychiatric illness, or healthy subjects, at a single time point or over multiple timepoints, by measuring blood Prostaglandin E2 (PGE2), PGF2α, or both, and C-Reactive Protein (CRP) concentrations in a sample, wherein the ratio of [PGE2]/[CRP] is indicative of the level of microglial activation in the brain of the one or more other subject(s) or group of subjects, for example one or more other subjects or groups of subjects having depression, OCD, another neuropsychiatric illness, or healthy subjects, at a single time point or over multiple timepoints. In addition, the ratio of blood [PGE2]/[CRP], [PGF2α]/[CRP], or both, of a test subject can be compared to the ratio of blood [PGE2]/[CRP], [PGF2α]/[CRP], or both, of one or more other subject(s) or group of subjects, for example one or more other subjects or groups of subjects having depression, OCD, another neuropsychiatric illness, or healthy subjects, at a single time point or over multiple timepoints. In such cases, a higher ratio of blood [PGE2]/[CRP], [PGF2α]/[CRP], or both, for the test subject compared to blood [PGE2]/[CRP], [PGF2α]/[CRP], or both, of the one or more other subject(s) or group of subjects, for example one or more other subjects or groups of subjects having depression, OCD, another neuropsychiatric illness, or healthy subjects, at a single time point or over multiple timepoints, may indicate a greater level of microglial activation in the brain of the test subject. In turn, without wishing to be bound by theory or limiting in any manner, the level of microglial activation in the brain of a subject is an index of brain inflammation. Thus, it follows that the greater level of microglial activation is an indication of a greater amount of brain inflammation in the test subject compared to the one or more other subjects or group of subjects.

Based on the information contained herein, the level of microglial activation may be used to identify, diagnose or assist in diagnosing a subject as having depression, a major depressive episode (MDE), a major depressive disorder (MDD), OCD, or other neuropsychiatric illness or that the subject is prone to developing depression, MDE, MDD, OCD, or other neuropsychiatric illness. Similarly, it is contemplated that the level of microglial activation and thus the blood [PGE2]/[CRP] and/or [PGF2α]/[CRP] ratios may be useful in determining or assisting in determining the degree of symptoms associated with depressive disorder, such as depression, MDE, MDD or another neuropsychiatric illness. Further, it is contemplated that the level of microglial activation and thus the blood [PGE2]/[CRP] ratio may be useful in determining or assisting in assessment of OCD in a subject.

The present invention also contemplates a method as described herein further comprising treating a subject with medication, non-medicinal therapy or a combination thereof, monitoring the subject, counseling the subject, testing or screening the subject for clinical depression, major depressive episode, major depressive disorder, OCD, or any other neuropsychiatric illness, testing the blood sample for one or more additional genetic markers, nucleotide sequences, proteins, metabolites or any combination thereof. Representative medicines that may be used to treat a subject include, without limitation, one or more antidepressants, anti-inflammatory agents, for example any agent or intervention which inhibits, reduces or prevents processes that participate in inflammation, an immunomodulator for example, any agent or intervention that changes the immune response or functioning of one or more immune functions, antipsychotics, mood stabilizers, anticonvulsants, antianxiolytics, or any combination thereof. Representative examples of antidepressant medication include Monoamine Oxidase Inhibitor (MAOIs) such as, but not limited to, tranylcypromine, phenelzine, isocarboxazid and the like, Tricyclic Antidepressants (TCAs) such as, but not limited to clomipramine, amitriptyline, desipramine, nortriptyline, doxepin, or trimipramine, Selective Serotonin Reuptake Inhibitors (SSRIs) such as, but not limited to citalopram, escitalopram, fluvoxamine, paroxetine, fluoxetine, sertraline or other common medications such as, but not limited to duloxetine, venlafaxine, mirtazapine, bupropion, trazodone, clozapine, lithium, ketamine any pharmaceutically acceptable salt or derivative thereof or any combination thereof. Other types of medicinal or non-medicinal therapy are further provided throughout the application including the claims.

It is also contemplated that a combination of medications may be employed to treat a subject or patient, for example, but not limited to an antidepressant in combination with an anti-inflammatory medication. Moreover, drug therapy may be employed with other therapeutic modalities.

In a preferred embodiment, prior to treating a subject, it is preferable that the subject has been diagnosed as being clinically depressed, having MDE, MDD or another neuropsychiatric illness by a qualified physician, or suspected of being clinically depressed or having MDE, MDD or another neuropsychiatric illness by a qualified physician, or has exhibited one or more symptoms of depression, MDE, MDD or one or more other neuropsychiatric illnesses.

In certain embodiments, subjects having OCD may be treated with a suitable conventional OCD treatment including a behavioral treatment, pharmaceutical treatment, or a combination thereof.

The present invention also contemplates a method of reducing microglial activation in the brain of a subject by administering to said subject an anti-inflammatory agent to reduce microglial activation in the subject. Without wishing to be bound by theory or limiting in any manner, it is believed an anti-inflammatory agent that can reduce microglial activation in the brain will in turn reduce brain inflammation and/or improve depressive disorders or symptoms associated therewith.

It is also contemplated that any of the methods described herein may further comprise a further step of brain imaging. In a preferred embodiment, the brain imaging is PET imaging. It is also contemplated that brain imaging may further comprising TSPO analysis of one or more regions of the brain, for example, but not limited to as described herein.

The present application also provides a kit comprising one or more markers of microglial activation, one or more markers of brain inflammation, one or more markers of peripheral body inflammation, one or more diagnostic agents capable of quantifying or assisting in quantifying one or more markers of microglial activation, one or more markers of brain inflammation, one or more markers of peripheral body inflammation or any combination thereof. The one or more diagnostic agents may comprise one or more antibodies or antibody derivatives such as, but not limited to FAB, FAB' or single chain antibodies or alternatively the agent may be any component, diluent or buffer which can be employed in mass spectrometry, HPLC, immunoassay, radioimmunoassay, gas chromatography-mass spectrometry or other chromatographic or non-chromatographic procedure to quantify the marker. In a preferred embodiment, the one or more markers of microglial activation are independently one or more of PGE2, PGF2α, and CRP from blood and the one or more diagnostic agents are independently one or more of an antibody against PGE2, an antibody against PGF2α, and an antibody against CRP. In an embodiment, a kit as described herein may include one or more of PGE2, PGF2α, and CRP as a positive control or calibrator.

The present invention also contemplates a kit comprising one or more components, such as, but not limited to one or more primary antibodies that are capable of binding to PGE2, PGF2α, or CRP, one or more secondary antibodies that are capable of binding the primary antibody, one or more solutions or reagents for immunological analysis, for example, blocking or binding solution or the like, a dish, multi-well plate or the like, purification media for example, but not limited to remove abundant plasma proteins from samples that are collected, centrifugation media, immunoabsorption columns, resin, buffers, enzymes, one or more supports, multiwell plates, instructions for using any component or practicing any method as described herein, or any combination thereof.

The results provided herein show that the ratio of PGE2 to CRP ([PGE2]/[CRP]) and the ratio of PGF2α to CRP ([PGF2α]/[CRP]) is elevated in the blood of patients with depressive disorders. The results also suggest that the levels of peripheral markers described herein correlate with depression and provide an index of inflammation in the brain. Thus the present invention also may be used for determining a subject's ratio of PGE2 to CRP, PGF2α to CRP, or both, in blood and if this or these ratio(s) is/are higher or elevated compared to a control group, in order to determine which subjects should be subjected to drug treatment, non-drug treatment, continued screening and/or monitoring, counseling, additional psychological testing, one or more genetic or other tests that predict, determine or diagnose depressive disorder or susceptibility thereto, and/or family screening. The present application also contemplates treating a patient with elevated PGE2/CRP levels, PGF2α/CRP levels, or both, using therapies known in the art in order to address symptoms associated with depressive disorder, improve mood, and/or prevent or reduce susceptibility to a depressive disorder or the symptoms associated therewith.

In another embodiment, there is provided herein a method for identifying candidates for treating brain inflammation in a subject having a neuropsychiatric illness, said method comprising: (a) measuring blood Prostaglandin E2 (PGE2), blood Prostaglandin F2α, or both, and C-Reactive Protein (CRP) pre-treatment concentrations in a pre-treatment sample obtained from the subject prior to administration of a potential agent for treating brain inflammation; (b) administering the potential agent for treating brain inflammation; and (c) measuring blood Prostaglandin E2 (PGE2), blood Prostaglandin F2α, or both, and C-Reactive Protein (CRP) post-treatment concentrations in a post-treatment sample obtained from the subject following administration of the potential agent for treating brain inflammation; wherein a reduction in [PGE2]/[CRP], [PGF2α]/[CRP], or both, post-treatment indicates that the potential agent is a candidate for treating brain inflammation in a subject having a neuropsychiatric illness.

The present invention will be further illustrated in the following examples.

EXAMPLES

Example 1: Increased Translocator Protein Distribution Volume, an In-Vivo Marker of Neuroinflammation, in the Brain During Major Depressive Episodes Participants Twenty subjects with a current major depressive episode (MDE) secondary to major depressive disorder (MDD) and 20 age-matched healthy participants completed the study. Participants were recruited from the Toronto area community and a tertiary care psychiatric hospital (Centre for Addiction and Mental Health, Toronto, Canada) between May 1, 2010 and Feb. 1, 2014. All were aged 18-70, non-smoking and in good physical health. None of the subjects had a history of autoimmune disease nor reported any recent illness. MDE subjects had early onset MDD (first MDE prior to age 45). Health or MDE was confirmed using the Structured Clinical Interview for DSM-V. Healthy participants were age-matched within 4 years to depressed patients. Exclusion criteria for all subjects included: being pregnant, any herbal, drug or medication use within six weeks, except for oral contraceptives, and any history of neurological illness or injury. All participants underwent urine drug screening and women received a urine pregnancy test on the PET scan day. All subjects provided written informed consent after all procedures were fully explained. The protocol and informed consent forms were approved by the Center for Addiction and Mental Health Research Ethics Board, Toronto, Canada.

Participants with MDE were administered the 17-item Hamilton Depression Rating Scale (HDRS) at enrollment and on the PET scan day. For enrollment, a minimum score of 17 on the 17-item HDRS was required. All MDE subjects were medication-free for at least 6 weeks prior to the PET scan day (9 subjects had completed one or more previous anti-depressant trials). Other exclusion criteria included concurrent active axis I disorders including current alcohol or substance dependence, MDE with psychotic symptoms, bipolar disorder (type I or II) and borderline or antisocial personality disorder. Depression severity was measured as the total score on the 17-item HDRS which is also strongly correlated with sickness behaviors of low mood and anhedonia (29). Additional measures taken were body mass index (BMI) and levels of several peripheral inflammatory markers in serum (interleukin-1β, interleukin-6, tumor necrosis factor α and C-reactive protein).

Image Acquisition and Analysis

Each participant underwent one [18F]FEPPA PET scan conducted at the Research Imaging Centre at the Centre for Addiction and Mental Health, Toronto, Canada. For this, intravenous [18F]FEPPA21 was administered as a bolus (mean±SD, 180.5±14.5 MBq or 4.88±0.4 mCi). [18F]FEPPA was of high radiochemical purity (>96%) and high specific activity (119±125 TBq/mmol). Manual and automatic (ABSS, Model #PBS-101 from Veenstra Instruments, Joure, The Netherlands) arterial blood samples were obtained to determine the ratio of radioactivity in whole blood to radioactivity in plasma, and the unmetabolized radioligand in plasma needed to create the input function for the kinetic analysis (30) The scan duration was 125 minutes following the injection of [18F]FEPPA. The PET images were obtained using 3D HRRT brain tomography (CPS/Siemens, Knoxville, Tenn., USA). All PET images were corrected for attenuation using a single photon point source, 137Cs (T½=30.2 years, Eg=662 keV) and were reconstructed by filtered back projection algorithm, with a HANN filter at Nyquist cutoff frequency (23).

Each subject underwent a 2D axial proton density magnetic resonance scan acquired with a General Electric (Milwaukee, Wis., USA) Signa 1.5 T magnetic resonance image scanner (slice thickness=2 mm, repetition time >5 300 ms, echo time=13 ms, flip angle=90 degree, number of excitations=2, acquisition matrix=256×256, and field of view=22 cm). Regions of interest were automatically generated using the in-house software, ROMI, as previously described (31) Time activity curves were used to estimate TSPO VT using a two-tissue compartment model, which has been shown previously to be an optimal model to quantitate TSPO VT with [18F]FEPPA PET (30).

DNA Extraction and Polymorphism Genotyping

The binding affinity of the second generation of radiotracers for TSPO, including [18F]FEPPA, is known to be affected by a co-dominantly expressed single nucleotide polymorphism (rs6971, C→T) in exon 4 of the TSPO gene (23, 24) High affinity binders (HAB, Ala147/Ala147) and mixed affinity binders (MAB, Ala147/Thr147) account for >90% of the population in North America (23). The polymorphism rs6971 was genotyped as described previously (23). One MDE subject was a low affinity binder (LB, Ala147/Thr147) and was not included in the analysis.

Statistical Analysis

PET data were analyzed by multivariate ANOVA with TSPO VT in PFC, ACC and insula as the dependent variables and diagnosis and genotype as fixed factors. Main effects were considered significant at the conventional P≤0.05. Effects in each region, analyzed by univariate ANOVA, were considered significant after Bonferroni correction (P≤0.017).

As a secondary analysis, a MANOVA including every brain region sampled (including all cortical and subcortical regions) was performed to assess the effect of diagnosis on TSPO VT. A partial correlation, controlling for rs6971 genotype, was used in a secondary analysis to quantitate the relationship between TSPO VT in the primary regions of interest and severity of symptoms of MDE measured by total HDRS score. HDRS score was missing in one MDE participant and was not included in this analysis. Partial correlations were considered significant at the Bonferroni corrected threshold of P≤0.008.

Results

A global effect of diagnosis on TSPO VT was observed (FIG. 1, Table 2). A MANOVA including all subregions of the prefrontal cortex as well as several other cortical and subcortical regions indicated a global brain effect of diagnosis with elevated TSPO VT in MDE compared to health (main effect of diagnosis, F15,23=4.46, P=0.001). Individuals in a MDE had significantly greater TSPO VT in prefrontal cortex (PFC), anterior cingulate cortex (ACC) and insula compared to healthy controls, after controlling for the effect of genotype (FIG. 1. Effect of diagnosis, MANOVA, F3,35=4.73, P=0.007. Effect of diagnosis, ANOVA by region: PFC, F1,37=8.07, P=0.007; ACC, F1,37=12.24, P=0.001; insula, F1,37=12.34, P=0.001; magnitude increases 26%, 32%, 33%, respectively). In both groups, the effect of the rs6971 polymorphism was significant (MANOVA, effect of genotype: F3,35=4.5, P=0.009) where HAB had higher TSPO VT compared to MAB. Scores on the HDRS indicated, on average, moderate to severe MDE (Table 1). Differences in TSPO VT between MDE and healthy subjects remained significant if age is applied as a covariate. The frequency of MAB and HAB rs6971 genotype expression was not significantly different between healthy subjects and those with MDE.

Figure 2:
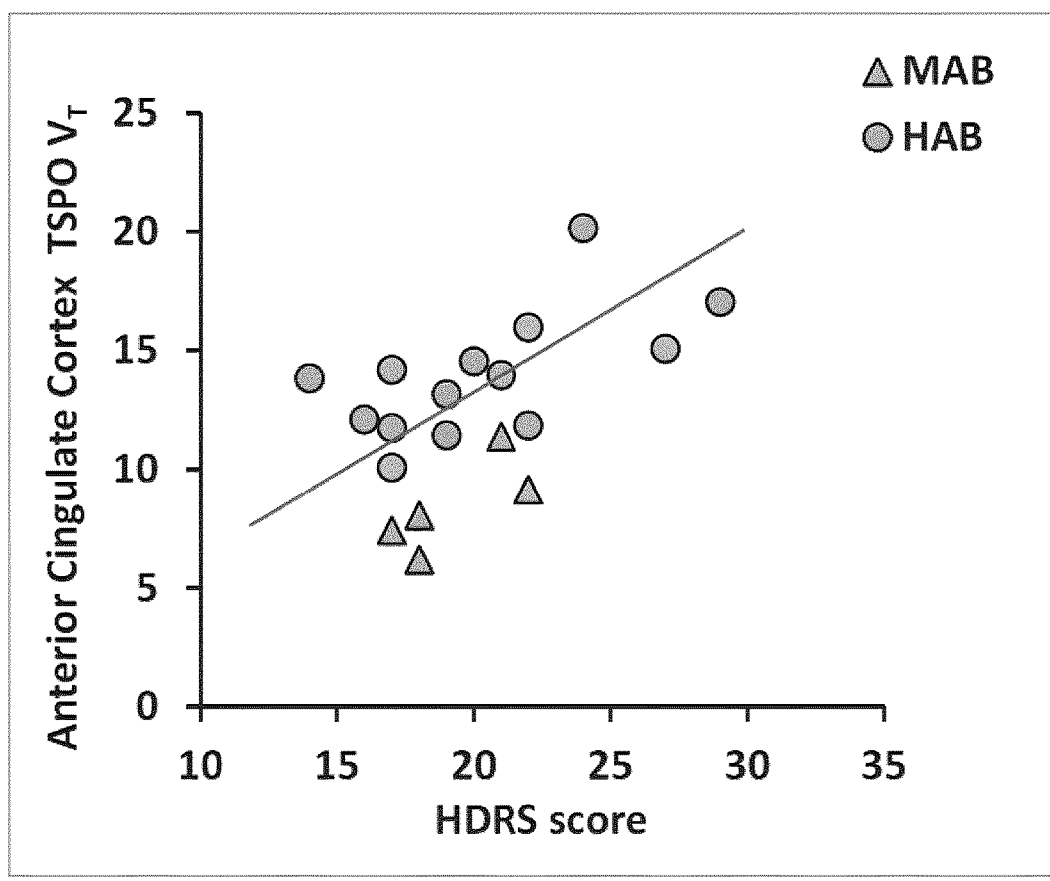
FIG. 2 shows the relationship between regional translocator protein density (TSPO VT) and symptoms of current major depressive episode. TSPO VT in the anterior cingulate cortex was positively related to scores on the 17-item Hamilton Depression Rating Scale (HDRS), after correcting for rs6971 genotype ($r=0.628$, $P=0.005$)

Total HDRS score, was positively correlated with TSPO VT in the ACC, after correcting for rs6971 genotype (r=0.628, P=0.005, FIG. 2). Similar correlations were found in the insula and PFC but these did not survive Bonferroni correction (insula, r=0.574, P=0.013; PFC, r=0.457, P=0.057).

In MDE subjects, but not healthy, BMI was significantly, negatively correlated with TSPO VT in the insula, after correcting for rs6971 genotype (r=−0.605, P=0.006,). The relationship between BMI and TSPO VT was also present in ACC (r=−0.547, P=0.015) and PFC (r=−0.488, P=0.034) but neither survived Bonferroni correction. In MDE subjects, none of the serum markers of inflammation had a significant positive correlation with TSPO VT in the primary regions of interest (see Table 3).

Discussion

This is the first study to detect microglial activation, as indicated by increased TSPO VT, in a substantial sample of MDE subjects. While the finding was prominent in the a priori regions of the PFC, ACC and insula, it was also present throughout all the regions assayed. Interestingly the highest levels of TSPO VT occurred in MDE subjects with the highest depression severity scores. These findings have important implications for the pathophysiology of MDE, identifying mechanisms contributing to symptom severity and weight loss in MDE, and clinical targeting of treatment.

Since TSPO is upregulated in activated microglia, elevated TSPO VT implies that greater microglial activation, a potentially targetable process of neuroinflammation, is present during MDE. During activation, microglia transform from a monitoring role into a macrophage-like state, responding to infections or insults, by phagocytosing pathogens and dying cells, and recruiting immune cells via cytokine secretion. However active microglia during MDE may represent a maladaptive response. Identifying greater microglial activation in MDE suggests that selective therapeutic strategies such as stimulating microglial targets like CX3CR1 to promote a more quiescent state, suppressing the effects of cytokines in the central nervous system, or promoting a shift in microglial activity towards repair oriented functions by activating purinergic receptors may hold promise (33). Reducing microglial activation itself is thought to have therapeutic utility and consistent with this viewpoint, minocycline, a second generation tetracycline antibiotic known to reduce microglial activation and TSPO expression in rodents (34, 35) can attenuate depressive behaviors in rodents (36). The present study also suggests that the ability of such interventions to reduce microglial activation may be monitored by techniques such as [18F]FEPPA PET or peripheral markers as described herein.

It was found that MDE was associated with elevated TSPO VT across all brain regions examined and regional TSPO VT was inter-correlated, although the relationships between TSPO VT with severity of MDE were most pronounced in the ACC. Without wishing to be bound by theory or limiting in any manner, while global mechanisms may account for elevated TSPO VT in multiple brain regions in MDD, greater TSPO VT in specific regions and/or their associated circuitry may be influential for the expression of particular symptoms within this complex disorder. As with any association between symptoms and a central biomarker the correlation found between higher TSPO VT and greater HDRS score in the ACC, can be interpreted as an epiphenomenon secondary to a common origin or that one phenomenon predisposes to the other. Without wishing to be considered limiting in any manner, we favor a causal mechanism of neuroinflammation contributing towards symptoms because induction of inflammation in humans is associated with depressed mood (26, 37) and direct induction of central inflammation in rodents is associated with anhedonia (7). The function of this region in relation to symptoms of MDE is consistent with this interpretation: The ACC participates in regulating and processing negative emotional responses (25). In MDD, active MDE symptoms are associated with higher metabolic function in the ACC and direct stimulation of the subgenual ACC results in reduction of MDE symptoms (25). The negative relationship between TSPO VT and BMI may be consistent with anorexia following induction of central inflammation (7). The insula is important in this relationship as it integrates interoceptive and affective signaling, is involved in homeostatically driven responses to food cues (27).

The lack of correlation between central and peripheral inflammatory markers is consistent with previous reports. Bromander et al., found no correlation between serum and cerebrospinal fluid TNF-α in neurosurgical patients (10). Similarly, dissociation between central and peripheral cytokines in preclinical data have been reported following peripheral (11, 12) or central inflammatory stimuli (13). It has been proposed that peripheral cytokines cross the blood brain barrier in severe medical illness to induce neuroinflammation and symptoms of depression (15). However, our results suggest that central inflammation may be present during MDE even when peripheral inflammation is absent.

This is the first study to find a significant elevation of brain TSPO density in vivo, a marker of microglial activation and neuroinflammation, during MDE. Though MDD has often been associated with increased peripheral inflammatory markers, the current study provides the first important compelling evidence for a neuroinflammatory process of microglial activation during MDE in a substantial group of subjects unbiased by other psychiatric illnesses or recent medication. Correlations found between greater regional TSPO density in the anterior cingulate cortex and insula with severity of MDE and BMI, respectively, may be explained by microglial activation leading to abnormal function in these regions contributing to symptoms.

Example 2: Peripheral Blood [PGE2]/[CRP] Correlates to Increased Translocator Protein Distribution Volume, an In-Vivo Marker of Neuroinflammation, in the Brain During Major Depressive Episodes Example 1 provides results suggesting that brain inflammation is present in clinical depression using a new advance in positron emission tomography. The imaging method is a scarce resource, requiring highly trained personnel to operate and costs about $5000 per scan. A low cost substitute marker would be highly desirable as approximately 1 in 3 people with clinical depression have brain inflammation. Further, about 4% of the general population are in the midst of a clinical depression so such a test could be useful for a substantial proportion of the general population. Present markers used by the depression research community do not actually relate to brain inflammation.

In the present Example, a different measure was employed to assess brain inflammation in blood than what has conventionally been done—a low molecular weight inflammatory marker (prostaglandin E2) that is made by activated microglia in the brain (the brain scan study showed that microglia are activated in clinical depression (see Example 1 for additional details)). This low molecular weight molecule was chosen due to its potential to pass out of the central nervous system into the periphery. Conventional thinking in the field is opposite to this approach.

A second issue addressed by the present Example is that inflammatory molecules made in the brain are also induced by inflammatory causing substances made in the periphery, and the periphery (in particular adipose tissue) can make the same inflammatory molecules secreted in brain. The peripheral blood sample represents both a brain contribution (comprising disease effect+stimulation of brain by periphery) plus a peripheral inflammation effect. So, to address this aspect, the instant application controls for peripheral influences that induce or create inflammatory molecules. In this regard, C-reactive protein was chosen to reflect the peripheral contribution towards inflammation as it is unlikely to pass across the blood brain barrier.

Figure 3:
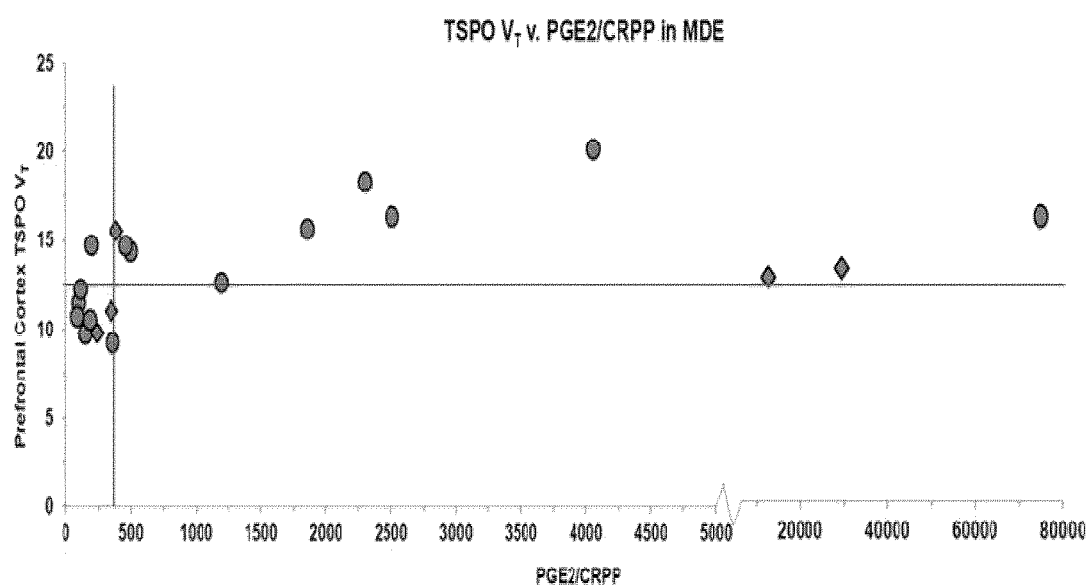
FIG. 3 shows the relationship between translocator protein density (TSPO VT) in the prefrontal cortex versus concentration of [PGE2]/[CRP] in subjects with major depressive episode. The vertical line intersecting the x-axis represents a threshold that would detect 11/12 patients with substantial inflammation as indicated by the horizontal line intersecting the y-axis.
Figure 4:
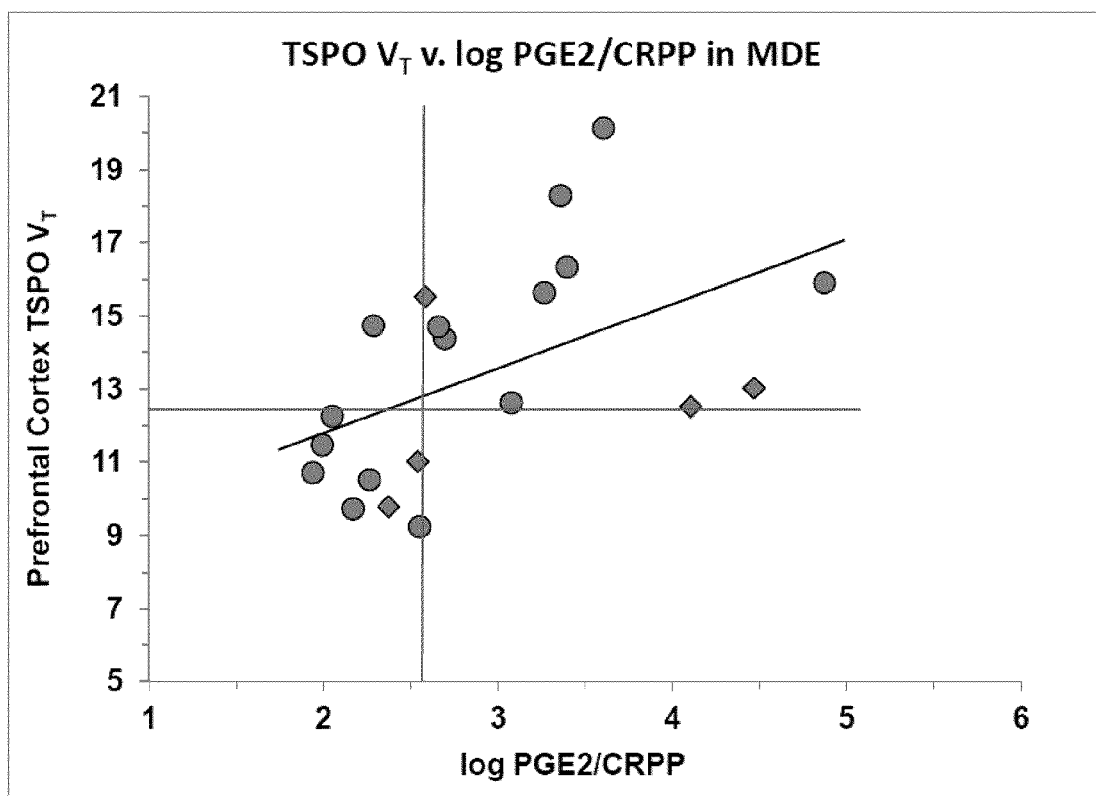
FIG. 4 shows the relationship between translocator protein density (TSPO VT) in the prefrontal cortex versus log concentration of [PGE2]/[CRP]. Pearson correlation: $r=0.513$, $P=0.021$, two tailed.

The relationship between translocator protein density (TSPO VT) in the prefrontal cortex versus blood concentration of [PGE2]/[CRP] in subjects with major depressive episode is shown in FIG. 3. The vertical line intersecting the x-axis represents a blood threshold that would detect 11/12 patients with substantial inflammation in the brain as indicated by the horizontal line intersecting the y-axis and suggests that the ratio of blood [PGE2]/[CRP] can be used as a marker or index brain inflammation. The relationship between translocator protein density (TSPO VT) in the prefrontal cortex versus log blood concentration of [PGE2]/[CRP is shown in FIG. 4 (Pearson correlation: r=0.513, P=0.021, two tailed).

Figure 5:
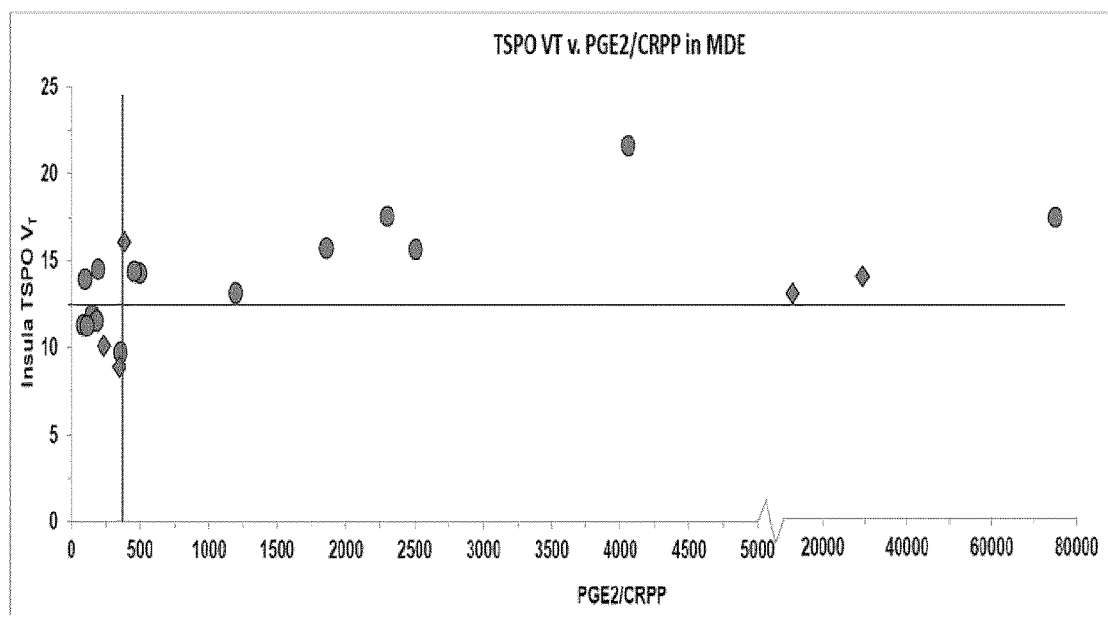
FIG. 5 shows the relationship between translocator protein density (TSPO VT) in the insula versus concentration of [PGE2]/[CRP] in subjects with major depressive episode. The vertical line intersecting the x-axis represents a threshold that would detect 10/12 patients with substantial inflammation as indicated by the horizontal line intersecting the y-axis.
Figure 6:
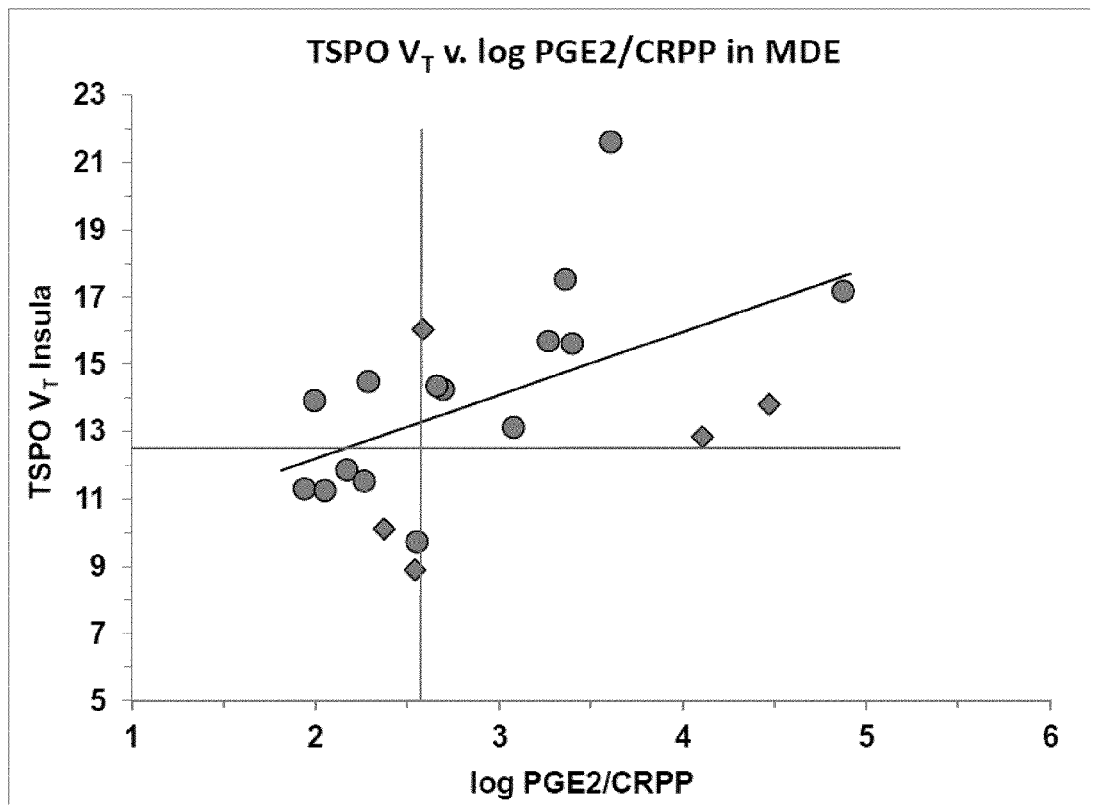
FIG. 6 shows the relationship between translocator protein density (TSPO VT) in the insula versus log concentration of [PGE2]/[CRP]. Pearson correlation: r=0.520, P=0.019, two tailed.

The relationship between translocator protein density (TSPO VT) in the insula versus blood concentration of [PGE2]/[CRP] in subjects with major depressive episode is shown in FIG. 5. The vertical line intersecting the x-axis represents a blood threshold that would detect 11/12 patients with substantial inflammation in the brain as indicated by the horizontal line intersecting the y-axis and again suggests that the ratio of blood [PGE2]/[CRP] can be used as a marker or index brain inflammation. The relationship between translocator protein density (TSPO VT) in the insula versus log blood concentration of [PGE2]/[CRP] is shown in FIG. 6 (Pearson correlation: r=0.520, P=0.019, two tailed.) Similar results (not shown) were observed for other brain regions as those discussed above.

The results presented indicate that (blood PGE2 concentration)/(blood C-reactive protein concentration) is highly predictive of microglial activation and thus this ratio represents a peripheral marker to detect microglial activation, a measure of brain inflammation. The results also provided indicate that increased brain inflammation is associated with depressive disorders and other neuropsychiatric disorders, for example, but not limited to MDE and MDD. Moreover, patients with the greatest [PGE2]/[CRP] ratios exhibited the highest depression scores as determined by DSM-V and Hamilton Depression Score rating. Thus, collectively, the results presented herein suggest that PGE2 and CRP may be employed as markers for neuropsychiatric diseases and/or brain inflammation occurring therewith and that the ratio of blood [PGE2]/[CRP] can be employed as an index of neuropsychiatric disease severity and/or brain inflammation occurring therewith.

Example 3: Peripheral Blood [PGE2]/[CRP] Correlates to Increased Translocator Protein Distribution Volume, an In-Vivo Marker of Neuroinflammation, in the Brain in Subjects Having Obsessive Compulsive Disorder (OCD)

Example 2 provides results indicating that peripheral blood [PGE2]/[CRP] correlates to increased TSPO VT in the brain during major depressive episodes. It was thus hypothesized that peripheral blood [PGE2]/[CRP] may correlate to other neuropsychiatric disorders and/or to brain inflammation occurring with other neuropsychiatric disorders as well. OCD is an example of a neuropsychiatric disorder which may be associated with, or diagnosed along with, MDD. Diagnosis is conventionally based on assessment of the symptoms experienced and the severity thereof. Conventional OCD diagnosis approaches are described in, for example, the diagnostic and statistical manual of mental disorders (DSM-5), which is herein incorporated by reference in its entirety. Peripheral markers correlating to OCD and/or to brain inflammation occurring with OCD, are desirable as they may facilitate or assist diagnosis and/or treatment, for example.

In the present example, the relationship between translocator protein density (TSPO VT) in the brain versus blood concentration of [PGE2]/[CRP] in subjects with OCD was assessed. TSPO VT in the subjects having OCD was assessed across three different regions of the brain, and the relationship between TSPO VT in each region and the blood concentration of [PGE2]/[CRP] in the subjects was determined.

Figure 7:
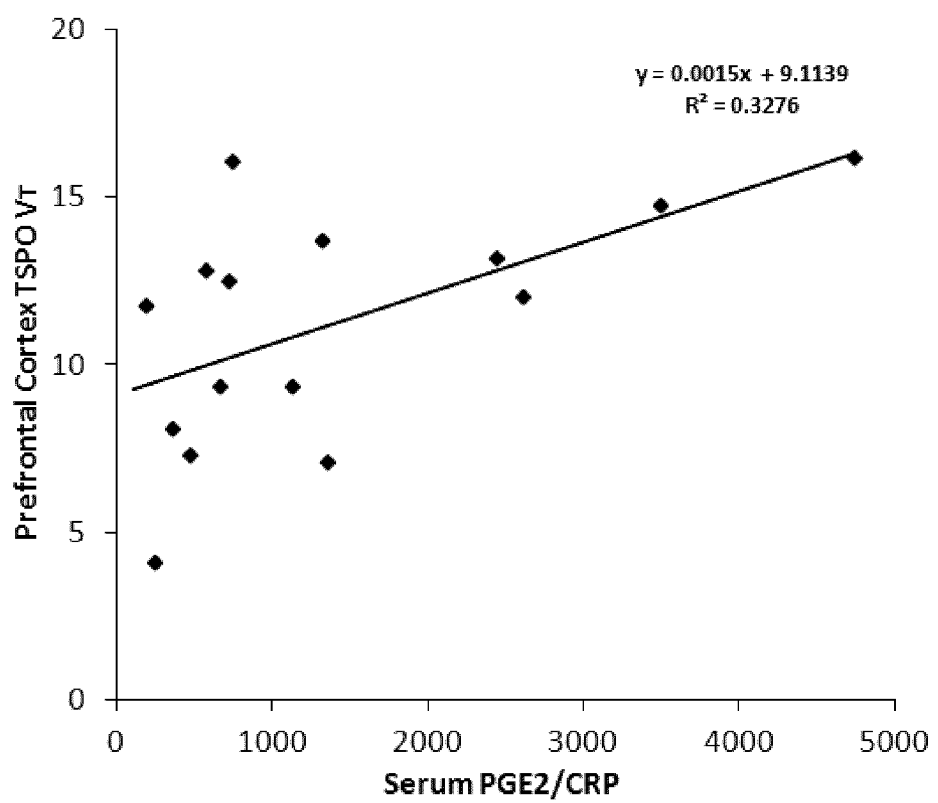
FIG. 7 shows the relationship between translocator protein density (TSPO VT) in the prefrontal cortex versus concentration of [PGE2]/[CRP] in subjects with OCD. Correlation: $r^2$=0.33, units for [PGE2] are ng/L, and units of [CRP] are mg/L. Sample consists of 15 subjects with obsessive compulsive disorder.
Figure 8:
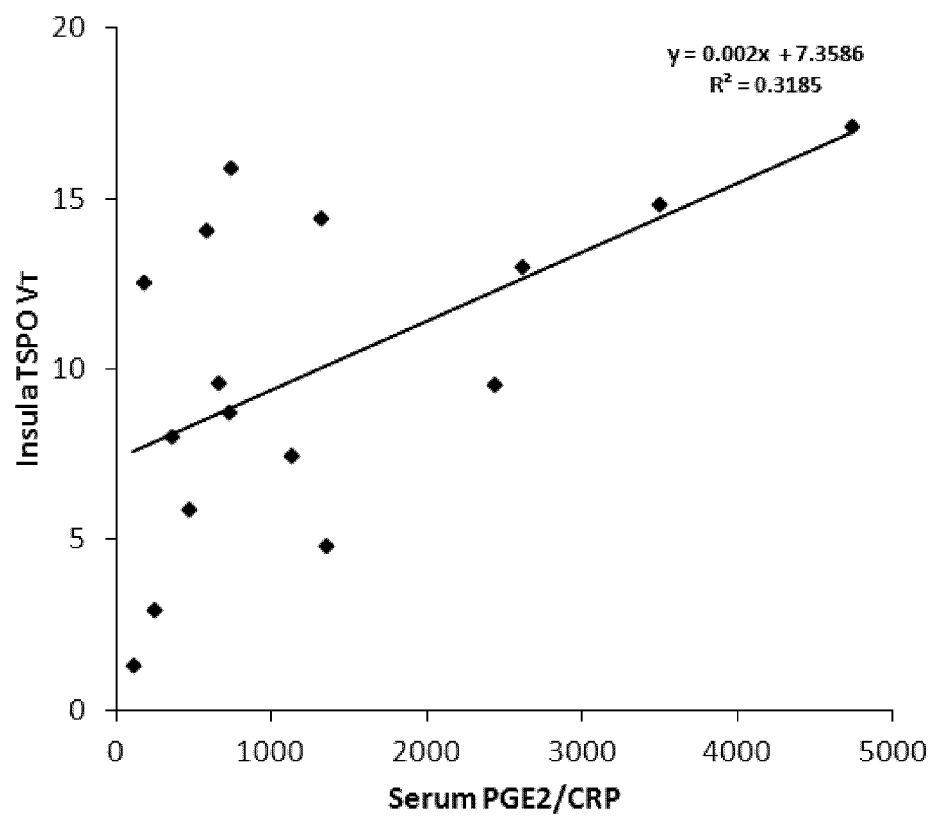
FIG. 8 shows the relationship between translocator protein density (TSPO VT) in the insula versus concentration of [PGE2]/[CRP] in subjects with OCD. Correlation: $r^2$=0.185. Units for [PGE2] are ng/L, and units of [CRP] are mg/L. Sample consists of 15 subjects with obsessive compulsive disorder.
Figure 9:
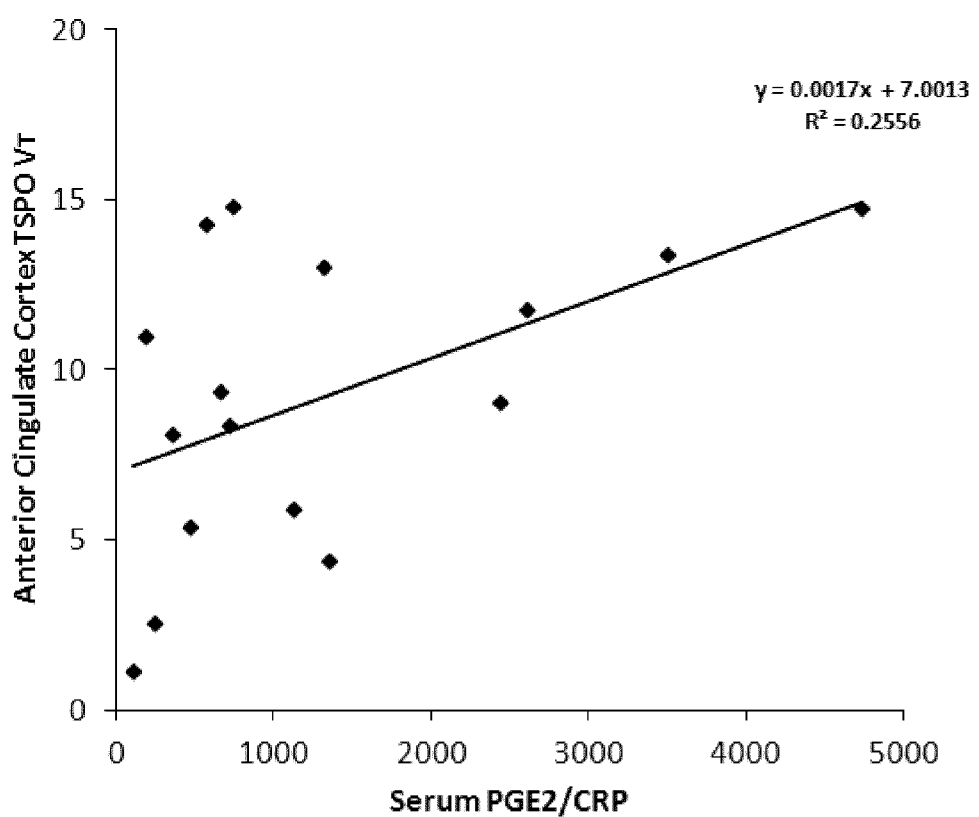
FIG. 9 shows the relationship between translocator protein density (TSPO VT) in the anterior cingulate cortex versus concentration of [PGE2]/[CRP] in subjects with OCD. Correlation: $r^2$=0.256, units for [PGE2] are ng/L, and units of [CRP] are mg/L. Sample consists of 15 subjects with obsessive compulsive disorder.

FIG. 7 shows the relationship between translocator protein density (TSPO VT) in the prefrontal cortex versus concentration of [PGE2]/[CRP] in the subjects with OCD. FIG. 8 shows the relationship between translocator protein density (TSPO VT) in the insula versus concentration of [PGE2]/[CRP] in the subjects with OCD. FIG. 9 shows the relationship between translocator protein density (TSPO VT) in the anterior cingulate cortex versus concentration of [PGE2]/[CRP] in the subjects with OCD.

Figure 10:
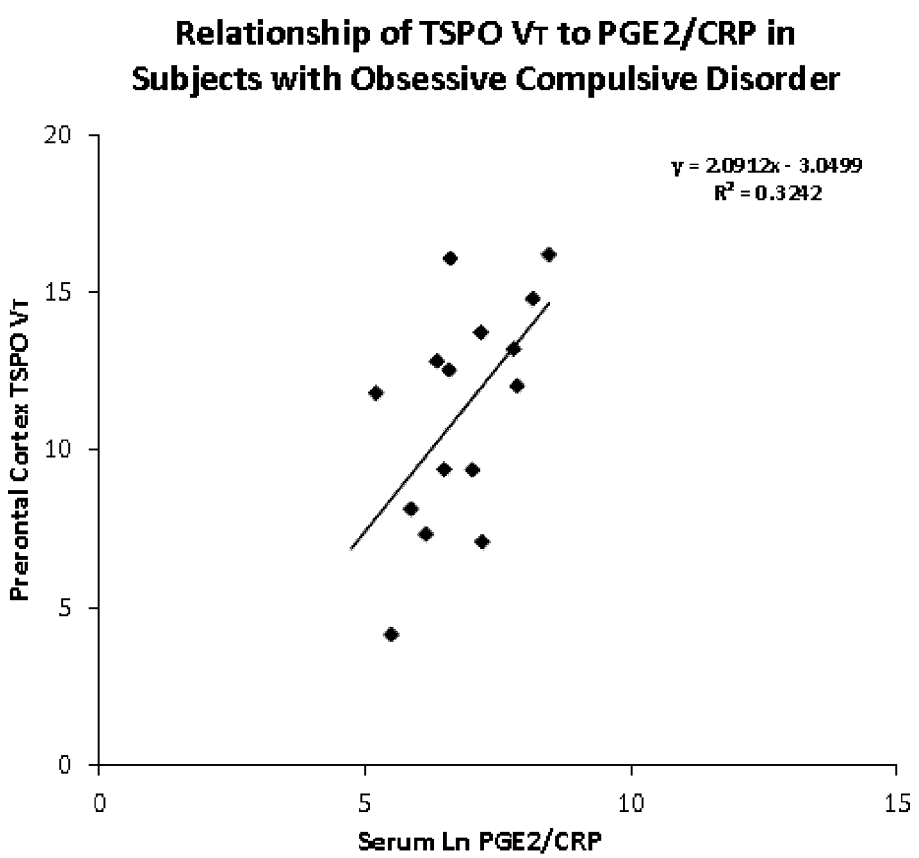
FIG. 10 shows the relationship between translocator protein density (TSPO VT) in the prefrontal cortex and ln[PGE2]/[CRP] in subjects with OCD. [PGE2] is in ng/L, [CRP] is in mg/L, correlation: $r^2$=0.3242. Sample consists of 15 subjects with OCD.
Figure 11:
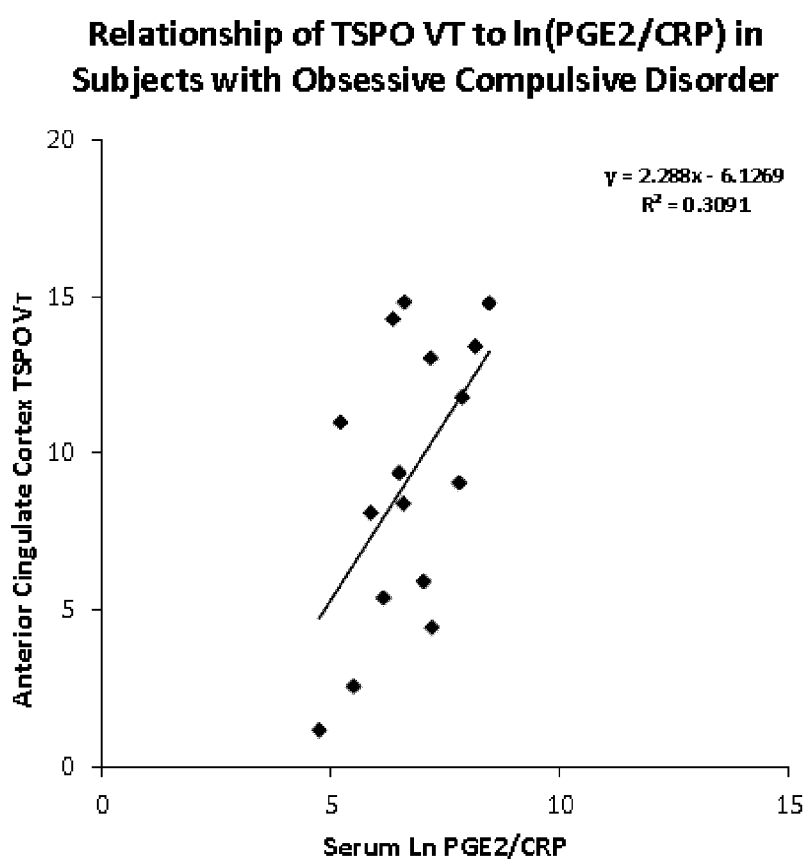
FIG. 11 shows the relationship between translocator protein density (TSPO VT) in the anterior cingulate cortex and ln[PGE2]/[CRP] in subjects with OCD. [PGE2] is in ng/L, [CRP] is in mg/L, correlation: $r^2$=0.3091. Sample consists of 16 subjects with OCD.

FIG. 10 shows the relationship between translocator protein density (TSPO VT) in the prefrontal cortex and ln[PGE2]/[CRP] (i.e., the natural log of [PGE2]/[CRP]) in subjects with OCD (sample size of 15). FIG. 11 shows the relationship between translocator protein density (TSPO VT) in the anterior cingulate cortex and ln[PGE2]/[CRP] (i.e., the natural log of [PGE2]/[CRP]) in subjects with OCD (sample consists of 16 subjects with OCD).

These results indicate that inflammation in the brain of subjects having OCD is correlated with the ratio of blood [PGE2]/[CRP], suggesting that the ratio of blood [PGE2]/[CRP] can be used as a marker or index of brain inflammation in subjects having OCD. Based on these results, the [PGE2]/[CRP] ratio in blood appears to be predictive of microglial activation in subjects having OCD, and thus this ratio represents a peripheral marker to detect microglial activation, a measure of brain inflammation, in subjects having OCD. Increased brain inflammation may be associated with neuropsychiatric disorders, as shown in previous examples herein for depression disorders. Thus, collectively, the results presented herein suggest that PGE2 and CRP may be employed as markers for neuropsychiatric diseases and/or markers for brain inflammation occurring with neuropsychiatric diseases.

Example 4: Peripheral Blood [PGF2α]/[CRP] Correlates to Increased Translocator Protein Distribution Volume, an In-Vivo Marker of Neuroinflammation, in the Brain in Subjects with Depression Examples 2 and 3 provide results indicating that PGE2 and CRP may be employed as markers for neuropsychiatric diseases and/or markers for brain inflammation occurring with neuropsychiatric diseases. It was thus hypothesized that certain other small molecules produced by microglia might also be useful markers. Prostaglandin F2α (PGF2α) is another member of the prostaglandin family to which PGE2 belongs, and is also produced by microglia.

In the present example, the relationship between translocator protein density (TSPO VT) in brain versus concentration of [PGF2α]/[CRP] in subjects with depression was assessed. TSPO VT in subjects having depression was assessed across three regions of the brain, and the relationship between TSPO VT in each region and the blood concentration of [PGF2α]/[CRP] in the subjects was determined.

Figure 12:
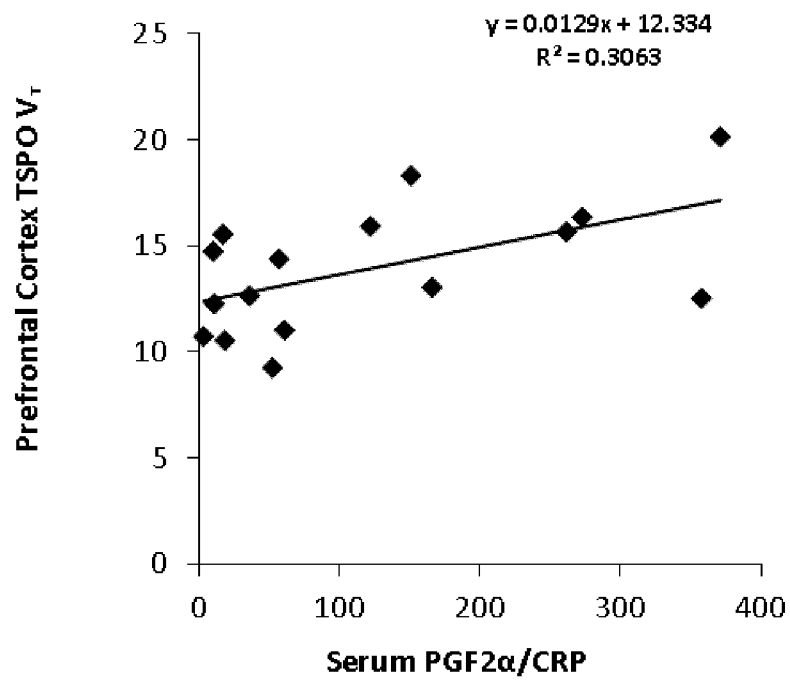
FIG. 12 shows the relationship between translocator protein density (TSPO VT) in the prefrontal cortex versus concentration of [PGF2α]/[CRP] in subjects with depression. Correlation: $r^2$=0.3063, units for [PGF2α] are ng/L, and units for [CRP] are mg/L. Sample consists of 16 subjects with depression.
Figure 13:
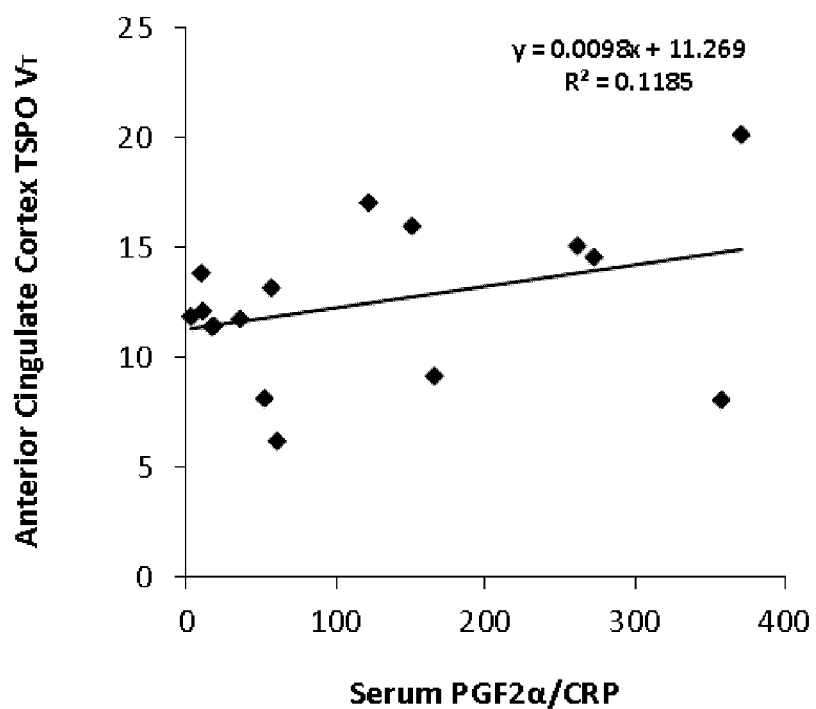
FIG. 13 shows the relationship between translocator protein density (TSPO VT) in the anterior cingulate cortex versus concentration of [PGF2α]/[CRP] in subjects with depression. Correlation: $r^2$=0.1185, units for [PGF2α] are ng/L, and units for [CRP] are mg/L. Sample consists of 16 subjects with depression.
Figure 14:
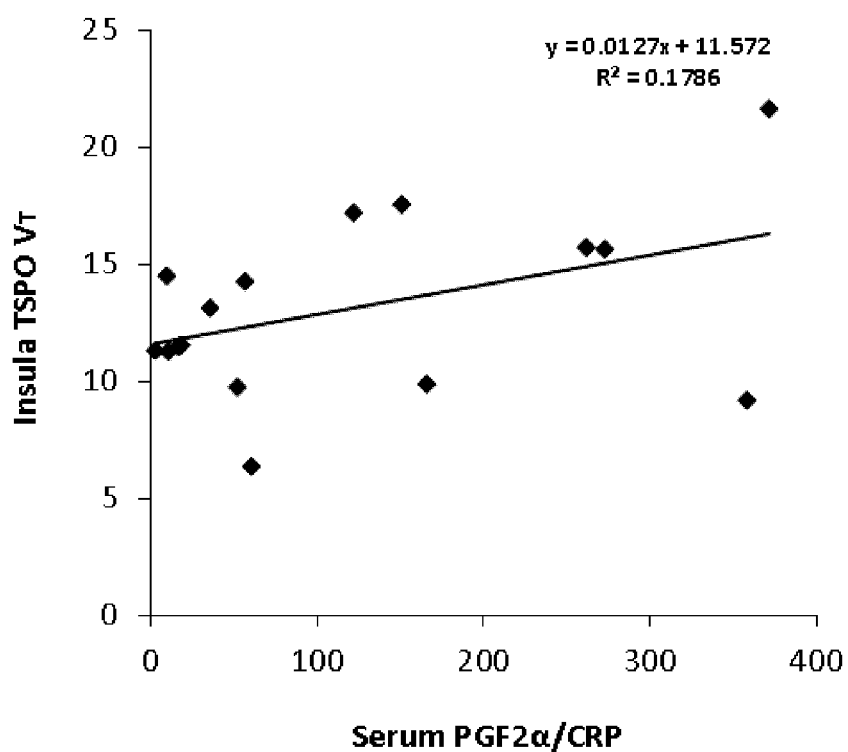
FIG. 14 shows the relationship between translocator protein density (TSPO VT) in the insula versus concentration of [PGF2α]/[CRP] in subjects with depression. Correlation: $r^2$=0.1786, units for [PGF2α] are ng/L, and units for [CRP] are mg/L. Sample consists of 16 subjects with depression.

FIG. 12 shows the relationship between translocator protein density (TSPO VT) in the prefrontal cortex versus concentration of [PGF2α]/[CRP] in subjects with depression (sample consists of 16 subjects with depression). FIG. 13 shows the relationship between translocator protein density (TSPO VT) in the anterior cingulate cortex versus concentration of [PGF2α]/[CRP] in the subjects with depression. FIG. 14 shows the relationship between translocator protein density (TSPO VT) in the insula versus concentration of [PGF2α]/[CRP] in the subjects with depression.

For some cutoff values, the positive predictive value of [PGF2α]/[CRP] in the subjects with depression is outstanding. By way of non-limiting example, selecting 12.5 on the TSPO VT y-axis as a high value (this value is about 25% elevated over a usual healthy level), then it can be seen that all subjects above this value have elevated prefrontal cortex TSPO VT, for example. In healthy subjects, it is uncommon to have a value of TSPO VT over 12.5%. Since 85% of healthy subjects fall below this value, it is meaningful. Approximately 15% of the general population (see Patten, S B, BMC Psychiatry, May 8, 9:19, 2009; herein incorporated by reference) will have a clinical depression over their lifespan, so a value exceeding 85% of healthy subjects is meaningful. As can further be seen, a high proportion of subjects having elevated TPSO VT exceed 100 on the x-axis, indicating that in this example an x-axis threshold of around 100, for example, may be considered as being of interest. The skilled person having regard to the teachings herein will understand that selection of thresholds of interest may vary as desired to suit particular examples or applications.

These results indicate that inflammation in the brain of subjects having depression is correlated with the ratio of blood [PGF2α]/[CRP], suggesting that the ratio of blood [PGF2α]/[CRP] can be used as a marker or index of brain inflammation in subjects having depression. Based on these results, the [PGF2α]/[CRP] ratio in blood appears to be predictive of microglial activation in subjects having depression, and thus this ratio represents a peripheral marker to detect microglial activation, a measure of brain inflammation, in subjects having depression. Increased brain inflammation may be associated with neuropsychiatric disorders, as shown in previous examples herein for depression disorders. Thus, collectively, the results presented herein suggest that PGF2α and CRP may be employed as markers for neuropsychiatric diseases and/or markers for brain inflammation occurring with neuropsychiatric diseases.

Examples 2 and 3 above demonstrate relationships between [PGE2]/[CRP] and brain inflammation. The present example indicates that yet another small molecule marker measurable in peripheral blood, [PGF2α]/[CRP], may represent an additional marker which may be employed as a marker for neuropsychiatric diseases and/or a marker for brain inflammation occurring with neuropsychiatric diseases, particularly depression.

Example 5: Peripheral Blood [PGF2α]/[CRP] and [PGE2]/[CRP] are Correlated in Subjects with Depression It will be recognized by the person of skill in the art having regard to the teachings herein that in certain examples, having more than one marker may be desirable. Having two markers may allow, for example, redundancy when performing assessments. One marker may serve as a positive control for the other, for example, increasing assessment confidence. An unexpected relationship finding between the two markers may signal that further testing may be performed to gain further insight. In certain examples, assessing more than one marker may allow for increased sensitivity, or a reduction in false negative determinations.

Examples 2 and 3 provide results indicating that PGE2 and CRP may be employed as markers for neuropsychiatric diseases and/or markers for brain inflammation occurring with neuropsychiatric diseases. Example 4 indicates yet another small molecule marker measurable in peripheral blood, [PGF2α]/[CRP], may represent an additional marker which may be employed as a marker for neuropsychiatric diseases and/or a marker for brain inflammation occurring with neuropsychiatric diseases, particularly depression.

It was thus hypothesized that assessment of both [PGE2]/[CRP] and [PGF2α]/[CRP], in combination, may be employed in the assessment of neuropsychiatric diseases and/or brain inflammation occurring with neuropsychiatric diseases. By way of example, if [PGE2]/[CRP] and [PGF2α]/[CRP] are correlated with one another in subjects having a neuropsychiatric disease, then it was hypothesized that both [PGE2]/[CRP] and [PGF2α]/[CRP] ratios may be used in the assessment of brain inflammation occurring with neuropsychiatric diseases, for example.

The relationship between [PGE2]/[CRP] and [PGF2α]/[CRP] was assessed in a sample of subjects with depression (sample size was N=16). Three subjects were observed as having very high values of [PGE2]/[CRP]. These high values are meaningful in that they are predictive of high TSPO VT, although they somewhat cloud the relationship between [PGE2]/[CRP] and [PGF2α]/[CRP] over subjects having less extreme [PGE2]/[CRP] values. Thus, the relationship between [PGE2]/[CRP] and [PGF2α]/[CRP] in the sample of subjects with depression was also assessed following exclusion of the three high values of [PGE2]/[CRP]. Here, a strong relationship between [PGE2]/[CRP] and [PGF2α]/[CRP] was seen with a correlation of about $r^2=0.885$.

Thus, in the results of this example, peripheral blood [PGF2α]/[CRP] and [PGE2]/[CRP] are correlated with one another in subjects with depression, particularly for subjects with depression in which [PGE2]/[CRP] values are below an extreme range. For example, an extreme [PGE2]/[CRP] value range may be above about 2000, 2100, 2200, 2300, 2400, 2500, 2600, 2700, 2800, 2900, 3000, 3100, 3200, 3300, 3400, 3500, 3600, 3700, 3800, 3900, or 4000, or any range therebetween or any integer value between about 2000 and 4000. It will be recognized that these ranges and values may be adjusted to suit particular applications.

All citations are hereby incorporated by reference.

The present invention has been described with regard to one or more embodiments. However, it will be apparent to persons skilled in the art that a number of variations and modifications can be made without departing from the scope of the invention as defined in the claims.

REFERENCES

1. Ustun T B, Ayuso-Mateos J L, Chatterji S, Mathers C, Murray CJ. Global burden of depressive disorders in the year 2000. Br J Psychiatry. 2004; 184:386-392.
2. Dwivedi Y. Brain-derived neurotrophic factor: role in depression and suicide. Neuropsychiatr Dis Treat. 2009; 5:433-449.
3. MacQueen G, Frodl T. The hippocampus in major depression: evidence for the convergence of the bench and bedside in psychiatric research? Mol Psychiatry. 2011; 16(3): 252-264.
4. Meyer J H. Neuroimaging markers of cellular function in major depressive disorder: implications for therapeutics, personalized medicine, and prevention. Clin Pharmacol Ther. 2012; 91(2):201-214.
5. Rajkowska G, Miguel-Hidalgo J J. Gliogenesis and glial pathology in depression. CNS Neurol Disord Drug Targets. 2007; 6(3):219-233.
6. Reichenberg A, Yirmiya R, Schuld A, Kraus T, Haack M, Morag A, Pollmacher T. Cytokine-associated emotional and cognitive disturbances in humans. Arch Gen Psychiatry. 2001; 58(5):445-452.
7. Fu X, Zunich S M, O'Connor J C, Kavelaars A, Dantzer R, Kelley K W. Central administration of lipopolysaccharide induces depressive-like behavior in vivo and activates brain indoleamine 2,3 dioxygenase in murine organotypic hippocampal slice cultures. J Neuroinflammation. 2010; 7:43.
8. Raison C L, Capuron L, Miller A H. Cytokines sing the blues: inflammation and the pathogenesis of depression. Trends Immunol. 2006; 27(1):24-31.
9. Maes M, Kubera M, Obuchowiczwa E, Goehler L, Brzeszcz J. Depression's multiple comorbidities explained by (neuro)inflammatory and oxidative & nitrosative stress pathways. Neuro Endocrinol Lett. 2011; 32(1):7-24.
10. Van Otterloo E S, Miguel-Hidalgo, J. J., Stockmeier, C., Rajkowska, G. Microglia immunoreactivity is unchanged in the white matter of orbitofrontal cortex in elderly depressed patients. Paper presented at: Society for Neuroscience, 2005; Washington, D.C.
11. Dean B, Tawadros N, Scarr E, Gibbons A S. Regionally-specific changes in levels of tumour necrosis factor in the dorsolateral prefrontal cortex obtained postmortem from subjects with major depressive disorder. J Affect Disord. 2010; 120(1-3):245-248.
12. Steiner J, Walter M, Gos T, Guillemin G J, Bernstein H G, Sarnyai Z, Mawrin C, Brisch R, Bielau H, Meyer zu Schwabedissen L, Bogerts B, Myint A M. Severe depression is associated with increased microglial quinolinic acid in subregions of the anterior cingulate gyrus: evidence for an immune-modulated glutamatergic neurotransmission? J Neuroinflammation. 2011; 8:94.
13. Shelton R C, Claiborne J, Sidoryk-Wegrzynowicz M, Reddy R, Aschner M, Lewis D A, Mimics K. Altered expression of genes involved in inflammation and apoptosis in frontal cortex in major depression. Mol Psychiatry. 2011; 16(7):751-762.
14. Sequeira A, Gwadry F G, Ffrench-Mullen J M, Canetti L, Gingras Y, Casero R A, Jr., Rouleau G, Benkelfat C, Turecki G. Implication of SSAT by gene expression and genetic variation in suicide and major depression. Arch Gen Psychiatry. 2006; 63(1):35-48.
15. Sibille E, Arango V, Galfalvy H C, Pavlidis P, Erraji-Benchekroun L, Ellis S P, John Mann J. Gene expression profiling of depression and suicide in human prefrontal cortex. Neuropsychopharmacology. 2004; 29 (2):351-361.
16. Steiner J, Bielau H, Brisch R, Danos P, Ullrich O, Mawrin C, Bernstein H G, Bogerts B. Immunological aspects in the neurobiology of suicide: elevated microglial density in schizophrenia and depression is associated with suicide. J Psychiatr Res. 2008; 42(2):151-157.
17. Pandey G N, Rizavi H S, Ren X, Fareed J, Hoppensteadt D A, Roberts R C, Conley R R, Dwivedi Y. Proinflammatory cytokines in the prefrontal cortex of teenage suicide victims. J Psychiatr Res. 2012; 46(1):57-63.
18. Rupprecht R, Papadopoulos V, Rammes G, Baghai T C, Fan J, Akula N, Groyer G, Adams D, Schumacher M. Translocator protein (18 kDa) (TSPO) as a therapeutic target for neurological and psychiatric disorders. Nat Rev Drug Discov. 2010; 9(12):971-988.
19. Bennacef I, Salinas, C., Horvath, G., Gunn, R., Bonasera, T., Wilson, A., Gee, A. and Laruelle, M. Comparison of [11C]PBR28 and [18F]FEPPA as CNS peripheral benzodiazepine receptor PET ligands in the pig. J Nucl Med. 2008; 49(Supplement 1):81P.
20. Kudo G, Toyama H, Hatano K, Suzuki H, Wilson A A, Ichise M, Ito F, Kato T, Katada K, Sawada M, Ito K. In-vivo imaging of microglial activation using a novel peripheral benzodiazepine receptor ligand, 18F-FEPPA and animal PET following 6-OHDA injury of the rat striatum; A comparison with 11C-PK11195. NeuroImage. 2008; 41(Supplement 2):T94-T94.
21. Wilson A A, Garcia A, Parkes J, McCormick P, Stephenson K A, Houle S, Vasdev N. Radiosynthesis and initial evaluation of [18F]-FEPPA for PET imaging of peripheral benzodiazepine receptors. Nucl Med Biol. 2008; 35(3): 305-314.
22. Hannestad J, DellaGioia N, Gallezot J D, Lim K, Nabulsi N, Esterlis I, Pittman B, Lee J Y, O'Connor K C, Pelletier D, Carson R E. The neuroinflammation marker translocator protein is not elevated in individuals with mild-tomoderate depression: a [(11)C]PBR28 PET study. *Brain Behav Immun.* 2013; 33:131-138.
23. Mizrahi R, Rusjan P M, Kennedy J, Pollock B, Mulsant B, Suridjan I, De Luca V, Wilson A A, Houle S. Translocator protein (18 kDa) polymorphism (rs6971) explains in-vivo brain binding affinity of the PET radioligand [(18)F]-FEPPA. *J Cereb Blood Flow Metab.* 2012; 32(6): 968-972.
24. Owen D R, Yeo A J, Gunn R N, Song K, Wadsworth G, Lewis A, Rhodes C, Pulford D J, Bennacef I, Parker C A, StJean P L, Cardon L R, Mooser V E, Matthews P M, Rabiner E A, Rubio J P. An 18-kDa translocator protein (TSPO) polymorphism explains differences in binding affinity of the PET radioligand PBR28. *J Cereb Blood Flow Metab.* 2012; 32(1):1-5.
25. Ressler K J, Mayberg H S. Targeting abnormal neural circuits in mood and anxiety disorders: from the laboratory to the clinic. *Nat Neurosci.* 2007; 10(9):1116-1124.
26. Hannestad J, Subramanyam K, Dellagioia N, Planeta-Wilson B, Weinzimmer D, Pittman B, Carson R E. Glucose metabolism in the insula and cingulate is affected by systemic inflammation in humans. *J Nucl Med.* 2012; 53(4):601-607.
27. Avery J A, Drevets W C, Moseman S E, Bodurka J, Barcalow J C, Simmons W K. Major Depressive Disorder Is Associated with Abnormal Interoceptive Activity and Functional Connectivity in the Insula. *Biol Psychiatry.* 2014; 76(3):258-266.
28. Simmons W K, Rapuano K M, Kallman S J, Ingeholm J E, Miller B, Gotts S J, Avery J A, Hall K D, Martin A. Category-specific integration of homeostatic signals in caudal but not rostral human insula. *Nat Neurosci.* 2013; 16(11):1551-1552.
29. Vrieze E, Demyttenaere K, Bruffaerts R, Hermans D, Pizzagalli D A, Sienaert P, Hompes T, de Boer P, Schmidt M, Claes S. Dimensions in major depressive disorder and their relevance for treatment outcome. *J Affect Disord.* 2014; 155:35-41.
30. Rusjan P, Wilson A A, Bloomfield P M, Vitcu I, Meyer J, Houle S, Mizrahi R. Quantification of translocator protein (18 kDa) in the human brain with PET and a novel radioligand, [18F]-FEPPA. *JCBFM* 2010; 31(8):1807-1816.
31. Chiuccariello L, Houle S, Miler L, Cooke R G, Rusjan P M, Rajkowska G, Levitan R D, Kish S J, Kolla N J, Ou X, Wilson A A, Meyer J H. Elevated monoamine oxidase a binding during major depressive episodes is associated with greater severity and reversed neurovegetative symptoms. *Neuropsychopharmacology.* 2014; 39(4):973-980.
32. Lawson L J, Perry V H, Dri P, Gordon S. Heterogeneity in the distribution and morphology of microglia in the normal adult mouse brain. *Neuroscience.* 1990; 39(1): 151-170.
33. Kierdorf K, Prinz M. Factors regulating microglia activation. *Front Cell Neurosci.* 2013; 7:44.
34. Martin A, Boisgard R, Kassiou M, Dolle F, Tavitian B. Reduced PBR/TSPO expression after minocycline treatment in a rat model of focal cerebral ischemia: a PET study using [(18)F]DPA-714. *Mol Imaging Biol.* 2011; 13(1):10-15.
35. He Y, Appel S, Le W. Minocycline inhibits microglial activation and protects nigral cells after 6-hydroxydopamine injection into mouse striatum. *Brain Res.* 2001; 909(1-2):187-193.
36. Henry C J, Huang Y, Wynne A, Hanke M, Himler J, Bailey M T, Sheridan J F, Godbout J P. Minocycline attenuates lipopolysaccharide (LPS)-induced neuroinflammation, sickness behavior, and anhedonia. *J Neuroinflammation.* 2008; 5:15.
37. Harrison N A, Brydon L, Walker C, Gray M A, Steptoe A, Critchley H D. Inflammation causes mood changes through alterations in subgenual cingulate activity and mesolimbic connectivity. *Biol Psychiatry.* 2009; 66(5): 407-414.
38. Lavisse S, Guillermier M, Herard A S, Petit F, Delahaye M, Van Camp N, Ben Haim L, Lebon V, Remy P, Dolle F, Delzescaux T, Bonvento G, Hantraye P, Escartin C. Reactive astrocytes overexpress TSPO and are detected by TSPO positron emission tomography imaging. *J Neurosci.* 2012; 32(32):10809-10818.

TABLE 1

Demographic Characteristics of Study Participants[a]

| Characteristics | Depressed (n = 20) | Healthy (n = 20) |
|---|---|---|
| Female, No. (%) | 12 (67) | 11 (55) |
| Age, y | 34.0 (11.3) | 33.6 (12.8) |
| TSPO Genotype[b] | 15 HAB, 5 MAB | 14 HAB, 6 MAB |
| BMI | 23.4 (5.4) | 24.8 (2.9) |
| HDRS Score[c] | 20.0 (3.8) | na |
| Age of first MDE, y | 15.7 (5.2) | na |
| Previous MDEs, No. | 6 (3) | na |
| Previous AD Trial, No. (%) | 9 (45) | na |
| No Previous AD Trial, No. (%) | 11 (55) | na |

[a]Values are expressed as mean (SD) except where indicated.
[b]Single nucleotide polymorphism rs6971 of the TSPO gene known to influence [18F] FEPPA binding: HAB, high affinity binders; MAB, mixed affinity binders.
[c]17-item Hamilton Depression Rating Scale; scores derived on the day of scanning. Missing data in one subject

TABLE 2

Analysis of Variance of Regional TSPO $V_T$ by Diagnosis and TSPO Genotype[a]

| Region of Interest | Depressed (n = 20) | | | Healthy (n = 20) | | | Diagnosis Effect[b] | | Genotype Effect[b] | |
|---|---|---|---|---|---|---|---|---|---|---|
| | HAB (n = 15) | MAB (n = 5) | Total | HAB (n = 14) | MAB (n = 6) | Total | $F_{1,37}$ | P | $F_{1,37}$ | P |
| MPFC | 13.6 (3.1) | 8.5 (2.0) | 12.3 (3.6) | 9.8 (2.1) | 8.3 (2.4) | 9.3 (2.2) | 11.4 | .002 | 11.2 | .002 |
| VLPFC | 14.9 (2.9) | 9.4 (1.7) | 13.5 (3.6) | 11.3 (2.4) | 9.5 (2.6) | 10.8 (2.5) | 9.1 | .005 | 13.5 | .001 |
| DLPFC | 13.6 (3.2) | 8.9 (1.3) | 12.4 (3.5) | 10.7 (2.3) | 8.8 (2.5) | 10.1 (2.5) | 6.5 | .015 | 11.6 | .002 |
| OFC | 14.4 (2.9) | 9.5 (2.7) | 13.2 (3.6) | 10.9 (2.4) | 9.6 (2.8) | 10.5 (2.5) | 7.8 | .008 | 9.4 | .004 |

TABLE 2-continued

Analysis of Variance of Regional TSPO $V_T$ by Diagnosis and TSPO Genotype[a]

| Region of Interest | Depressed (n = 20) | | | Healthy (n = 20) | | | Diagnosis Effect[b] | | Genotype Effect[b] | |
|---|---|---|---|---|---|---|---|---|---|---|
| | HAB (n = 15) | MAB (n = 5) | Total | HAB (n = 14) | MAB (n = 6) | Total | $F_{1,37}$ | P | $F_{1,37}$ | P |
| Frontal Pole | 13.3 (3.0) | 8.9 (2.0) | 12.2 (3.3) | 10.2 (2.1) | 8.3 (2.3) | 9.6 (2.3) | 9.1 | .005 | 11.8 | .002 |
| ACC | 13.5 (2.9) | 8.4 (2.0) | 12.3 (3.5) | 9.8 (2.0) | 8.0 (2.3) | 9.3 (2.2) | 12.2 | .001 | 14.2 | .001 |
| Insula | 14.2 (3.0) | 8.8 (2.1) | 12.9 (3.7) | 10.2 (2.2) | 8.6 (2.5) | 9.7 (2.3) | 12.3 | .001 | 12.6 | .001 |
| Temporal Cortex | 14.4 (2.8) | 8.7 (2.1) | 12.9 (3.6) | 10.9 (2.2) | 9.0 (2.5) | 10.3 (2.4) | 8.7 | .006 | 15.9 | .000 |
| Parietal Cortex | 15.0 (3.1) | 9.6 (2.0) | 13.7 (3.7) | 11.5 (2.2) | 9.6 (2.5) | 10.9 (2.4) | 8.9 | .005 | 13.8 | .001 |
| Occipital Cortex | 14.5 (3.0) | 8.4 (2.2) | 12.9 (3.9) | 11.0 (2.1) | 9.3 (2.7) | 10.5 (2.4) | 7.0 | .012 | 14.8 | .000 |
| Hippocampus | 12.8 (2.5) | 7.9 (2.7) | 11.5 (3.3) | 9.4 (2.3) | 8.6 (2.3) | 9.2 (2.3) | 7.5 | .009 | 9.4 | .004 |
| Thalamus | 16.9 (3.6) | 10.2 (2.2) | 15.2 (4.4) | 11.8 (2.2) | 10.4 (2.9) | 11.4 (2.4) | 13.6 | .001 | 12.5 | .001 |
| Dorsal Putamen | 12.3 (2.6) | 7.3 (1.5) | 11.1 (3.2) | 8.5 (1.6) | 7.5 (2.3) | 8.2 (1.8) | 14.1 | .001 | 12.4 | .001 |
| Dorsal Caudate | 10.9 (2.6) | 6.4 (1.8) | 9.8 (3.1) | 8.2 (1.9) | 6.7 (2.1) | 7.8 (2.0) | 6.7 | .013 | 13.4 | .001 |
| Ventral Striatum | 12.2 (3.2) | 7.4 (2.3) | 11.0 (3.7) | 9.0 (1.8) | 7.9 (2.1) | 8.7 (2.0) | 6.9 | .013 | 9.2 | .004 |

[a]Values are expressed as mean (SD).
[b]Main effect of univariate ANOVA.
MPFC, medial prefrontal cortex; VLPFC, ventrolateral prefrontal cortex; DLPFC, dorsolateral prefrontal cortex; OFC, orbitofrontal cortex; ACC, anterior cingulate cortex.
HAB, high affinity binders and MAB, mixed affinity binders refer to the single nucleotide polymorphism rs6971 of the TSPO gene known to influence [$^{18}$F]FEPPA binding.
For a more detailed description of the subregions of the prefrontal cortex please refer to the supplemental section.

TABLE 3

Correlation Between Regional TSPO $V_T$ and Peripheral Inflammatory Markers in Major Depressive Episodes

| Marker | Prefrontal Cortex | Anterior Cingulate Cortex | Insula |
|---|---|---|---|
| IL-1β | −0.35 (0.13)[a] | −0.39 (0.09) | −0.35 (0.14) |
| IL-6 | −0.20 (0.39) | −0.04 (0.88) | −0.09 (0.70) |
| TNFα | −0.29 (0.21) | −0.34 (0.14) | −0.36 (0.12) |
| CRP | −0.27 (0.25) | −0.16 (0.51) | −0.26 (0.27) |
| *Correlations Controlling for rs6971 Genotype* | | | |
| IL-1β | −0.39 (0.10) | −0.45 (0.05) | −0.40 (0.09) |
| IL-6 | −0.29 (0.24) | −0.08 (0.75) | −0.15 (0.53) |
| TNFα | −0.33 (0.16) | −0.40 (0.09) | −0.44 (0.06) |
| CRP | −0.52 (0.02) | −0.40 (0.09) | −0.54 (0.02) |
| *Correlations Controlling for Body Mass Index* | | | |
| IL-1β | −0.18 (0.46) | −0.21 (0.38) | −0.14 (0.56) |
| IL-6 | −0.12 (0.62) | 0.09 (0.71) | 0.03 (0.89) |
| TNFα | 0.18 (0.46) | 0.16 (0.52) | 0.18 (0.46) |
| CRP | −0.15 (0.54) | 0.01 (0.98) | −0.12 (0.63) |
| *Correlations Controlling for Both rs6971 Genotype and Body Mass Index* | | | |
| IL-1β | −0.25 (0.31) | −0.31 (0.21) | −0.23 (0.36) |
| IL-6 | −0.22 (0.39) | 0.04 (0.87) | −0.04 (0.89) |
| TNFα | 0.05 (0.84) | 0.01 (0.97) | 0.03 (0.90) |
| CRP | −0.42 (0.08) | −0.25 (0.31) | −0.43 (0.07) |

[a]Values represent the correlation coefficient (or partial correlation coefficient) followed by the two tailed, uncorrected p-value. Positive r values would reflect greater TSPO $V_T$ when a higher plasma level of the peripheral marker is present. Body mass index (BMI) was included in two analyses since all of these serum markers are also secreted by adipocytes.

What is claimed is:

1. A method of treatment, which comprises:
   determining a level of microglial activation in the brain of a subject by measuring blood Prostaglandin E2 (PGE2) and C-Reactive Protein (CRP) concentrations in a blood sample obtained from the subject, wherein the ratio of blood PGE2 concentration divided by blood CRP concentration ([PGE2]/[CRP]) is indicative of the level of microglial activation in the brain of the subject; and
   treating the subject with an anti-inflammatory agent and/or antidepressant when the [PGE2]/[CRP] is greater than 250.

2. The method of claim 1, wherein the blood sample is a serum sample obtained from the subject and PGE2 and CRP concentrations are measured from blood, serum, or plasma in the sample.

3. The method of claim 1, wherein the subject is depressed.

4. The method of claim 3, wherein the subject is clinically depressed.

5. The method of claim 4, wherein the subject is diagnosed with or has major depressive episode (MDE) or major depressive disorder (MDD).

6. The method of claim 4, wherein the subject exhibits major depressive episode (MDE) secondary to major depressive disorder (MDD).

7. The method of claim 3, wherein the subject has obsessive compulsive disorder (OCD).

8. The method of claim 1, wherein the blood PGE2 and blood CRP concentrations are quantified by mass spectrometry, HPLC, immunoassay, radioimmunoassay or gas chromatography-mass spectrometry.

* * * * *